US010994091B2

(12) United States Patent
McKenna et al.

(10) Patent No.: US 10,994,091 B2
(45) Date of Patent: May 4, 2021

(54) ADSORBENT CARTRIDGE WITH ACCURATE VISUAL INDICATOR

(71) Applicant: Micropore, Inc., Elkton, MD (US)

(72) Inventors: Douglas B. McKenna, Avondale, PA (US); Vince Suddard, Newark, DE (US); Glenn Shealy, Hockessin, DE (US)

(73) Assignee: Micropore, Inc., Elkton, MD (US)

( * ) Notice: Subject to any disclaimer, the term of this patent is extended or adjusted under 35 U.S.C. 154(b) by 0 days.

(21) Appl. No.: 16/343,705

(22) PCT Filed: Oct. 20, 2017

(86) PCT No.: PCT/US2017/057592
§ 371 (c)(1),
(2) Date: Apr. 19, 2019

(87) PCT Pub. No.: WO2018/075891
PCT Pub. Date: Apr. 26, 2018

(65) Prior Publication Data
US 2019/0262573 A1    Aug. 29, 2019

Related U.S. Application Data

(60) Provisional application No. 62/411,409, filed on Oct. 21, 2016.

(51) Int. Cl.
*A61M 16/10* (2006.01)
*B01D 53/04* (2006.01)
(Continued)

(52) U.S. Cl.
CPC ........ *A61M 16/105* (2013.01); *A61M 16/104* (2013.01); *A61M 16/22* (2013.01);
(Continued)

(58) Field of Classification Search
None
See application file for complete search history.

(56) References Cited

U.S. PATENT DOCUMENTS

| 3,068,073 A | 12/1962 | Stanford |
| 4,326,514 A | 4/1982 | Eian |

(Continued)

FOREIGN PATENT DOCUMENTS

RU    2489184    8/2013

OTHER PUBLICATIONS

Lillo, et al., "Chemical safety of U.S. Navy Fleet soda lime," Undersea Hyperb. Med., 1996, 23(1):43-53.
(Continued)

*Primary Examiner* — Jelitza M Perez
(74) *Attorney, Agent, or Firm* — Fish & Richardson P.C.

(57) ABSTRACT

A cartridge comprising layers of adsorbent sheet is described. The cartridge includes an indicator that characterizes the consumption state of the adsorbent within the cartridge. The indicator is applied in a way such that discrete areas of indicator are visible. These discontinuous areas of indicator may be applied to the outside surface of the cartridge. Alternatively, the discontinuous areas may be formed by cutting windows in the outermost layer of the cartridge and either coating indicator on the layer beneath the window, placing an indicator layer between the window and the layer beneath it or filling the window with an indicating plug of material so that the indicator is visible from the outside of the cartridge. The indicator layer and indicator plug embodiments allow the use of any indicator with any adsorbent.

18 Claims, 14 Drawing Sheets

0 Hours, end of test      22 Hours      42 Hours      75 Hours

(51) Int. Cl.
    *B01J 20/04*     (2006.01)
    *B01J 20/08*     (2006.01)
    *B01J 20/22*     (2006.01)
    *B01J 20/26*     (2006.01)
    *B01J 20/28*     (2006.01)
    *A61M 16/22*     (2006.01)
    *A62B 19/00*     (2006.01)
    *B01D 35/143*     (2006.01)
    *A62B 18/08*     (2006.01)

(52) U.S. Cl.
    CPC .......... *A62B 19/00* (2013.01); *B01D 53/0415* (2013.01); *B01J 20/041* (2013.01); *B01J 20/08* (2013.01); *B01J 20/22* (2013.01); *B01J 20/26* (2013.01); *B01J 20/28033* (2013.01); *B01J 20/28052* (2013.01); *A61M 2016/103* (2013.01); *A61M 2205/584* (2013.01); *A62B 18/088* (2013.01); *B01D 35/143* (2013.01); *B01D 2253/112* (2013.01); *B01D 2257/504* (2013.01); *B01D 2259/4533* (2013.01)

(56) References Cited

U.S. PATENT DOCUMENTS

| | | |
|---|---|---|
| 4,985,296 A | 1/1991 | Mortimer |
| 5,109,838 A | 5/1992 | Elam |
| 5,124,129 A | 6/1992 | Riccitelli et al. |
| 5,766,312 A | 6/1998 | Furhmann et al. |
| 5,964,221 A | 10/1999 | McKenna |
| 7,326,280 B2 | 2/2008 | Hrycak et al. |
| 7,329,307 B2 | 2/2008 | Hrycak et al. |
| 7,442,237 B1 | 10/2008 | Gardner |
| 7,476,641 B2 | 1/2009 | Holder |
| 8,413,655 B2 | 4/2013 | McKenna et al. |
| 8,685,153 B2 | 4/2014 | McKenna et al. |
| 8,821,619 B2 * | 9/2014 | McKenna .......... B01D 53/0415 55/498 |
| 2004/0048742 A1 | 3/2004 | Chin |
| 2005/0160913 A1 | 7/2005 | Hrycak |
| 2006/0254973 A1 | 11/2006 | Olsen et al. |
| 2007/0251390 A1 | 11/2007 | Lombardi |
| 2007/0251391 A1 | 11/2007 | Thomas |
| 2010/0006505 A1 | 1/2010 | Smith et al. |
| 2011/0068053 A1 | 3/2011 | Kim et al. |
| 2012/0090470 A1 | 4/2012 | McKenna |
| 2014/0205505 A1 | 7/2014 | Kirollos et al. |
| 2016/0030877 A1 | 2/2016 | Frankel |

OTHER PUBLICATIONS

EP Office Action in European Appln. No. 17862469.8, dated Sep. 18, 2019, 7 pages.
Miller's Anesthesia, vol. 1, 8th Ed., Miller, 2015, pp. 788-790.
PCT International Preliminary Report on Patentability in International Appln. No. PCT/US2017/057592, dated Apr. 23, 2019, 5 pages.
PCT International Search Report and Written Opinion in International Appln. No. PCT/US2017/057592, dated Jan. 16, 2018, 7 pages.

* cited by examiner

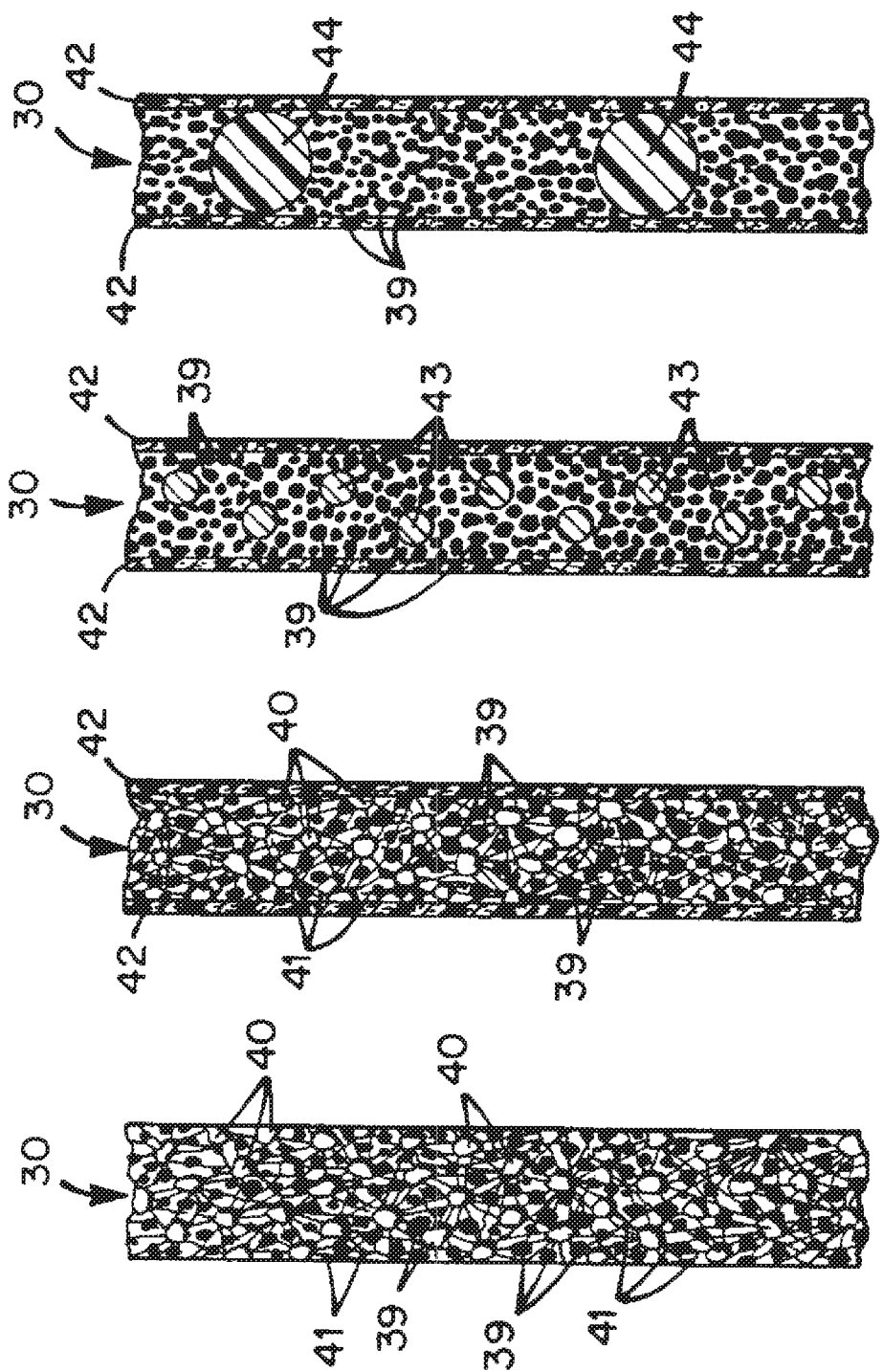

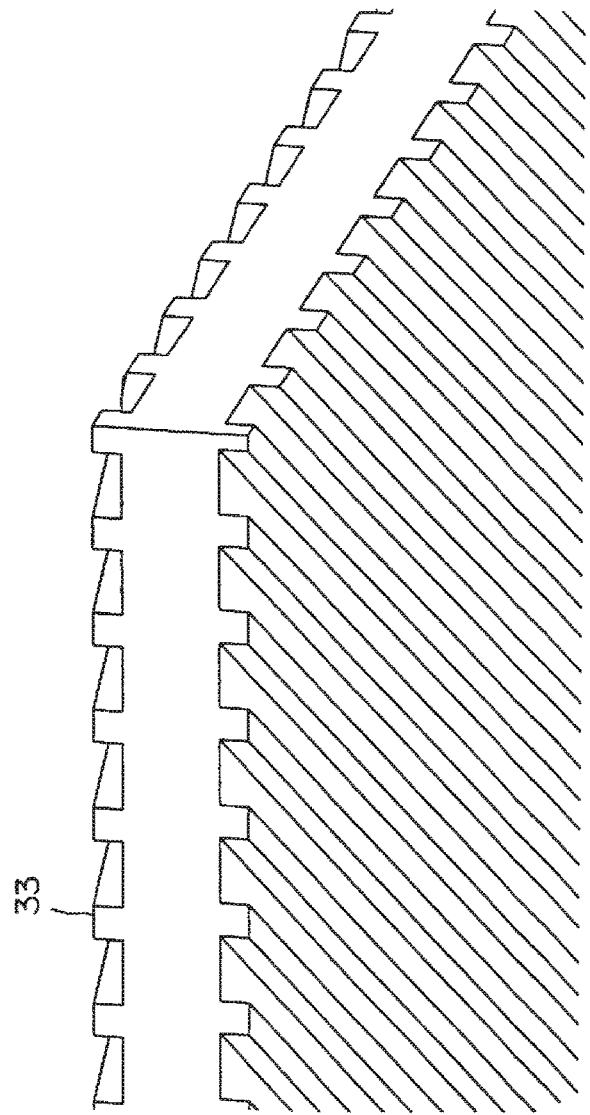

ADSORBENT CARTRIDGE WITH ACCURATE VISUAL INDICATOR

This application is a 371 of International Application No. PCT/US2017/057592, filed Oct. 20, 2017, which claims the benefit of priority of U.S. Provisional Application No. 62/411,409, filed Oct. 21, 2016, which are incorporated herein by reference in its entirety.

TECHNICAL FIELD

This application relates to adsorbent cartridges having discrete areas of visual indicator for indicating the consumption state of the adsorbent within the cartridge in an accurate manner.

BACKGROUND

During surgical procedures anesthetic agent may not be entirely consumed and in such cases air exhausted by the patient can be recycled. This allows for the efficient use of anesthetic, as well as avoiding needless release to the atmosphere, where many anesthetic agents can contribute to global warming. In order for a patient to rebreathe their exhausted air, exhaled $CO_2$ must be adsorbed. This is achieved by passing the recycled air through a $CO_2$ adsorbent comprising calcium hydroxide or lithium hydroxide or mixtures thereof (sodium hydroxide is often used in combination with calcium hydroxide to catalyze the reaction to calcium carbonate). In order to determine how much of the adsorbent has been reacted, granular adsorbent materials are typically coated with as little as 0.001 w/w % indicator dye that changes color when the absorbent is reacted (U.S. Pat. No. 7,476,641). In the case of calcium hydroxide, the color change occurs because of the decrease in pH due to the conversion of calcium hydroxide to calcium carbonate, as well as the short term consumption of sodium hydroxide. This lowers the pH to less than 10.3, causing an ethyl violet indictor to turn from clear to purple. By monitoring how much of the adsorbent has been converted, the anesthesiologist can determine how much time is available before the adsorbent must be changed. Indicator also allows decisions to be made between procedures as to whether adsorbent beds should be changed before the next procedure.

One problem with existing granular absorbents is that the indicating chemistry may be a contaminant, and this contaminant is currently mixed in throughout all of the adsorbent. The US Navy uses calcium hydroxide $CO_2$ adsorbents for military rebreather diving, and reported an incident where amine odors were observed with the use of color indicating granular adsorbents (https://www.ncbi.nlm.nih.gov/pubmed/8653065).

Methods have been proposed to put indicator not in the adsorbent, but rather in thin layers between the adsorbent and an outer transparent wall of the canister that holds the adsorbent (U.S. Pat. Nos. 4,326,514; 5,109,838). This does not, however, address another issue with granular adsorbents. Improperly packed beds or beds that settle during shipping can lead to gas channeling (Miller, R. D. et. al., Miller's Anesthesia, vol. 1. 2015, Elsevier, p. 788-790) and therefore a non-uniform reaction zone (FIG. 2), which makes it difficult to objectively determine when the granular bed is spent. Adsorbent canisters are therefore often pulled well before all of the adsorbent is utilized, to prevent the possibility of patient exposure to excessive levels of carbon dioxide due to early breakthrough. The use of indicating layers on the outside of an adsorbent bed does not give information on potential gas channeling and early breakthrough inside the bed.

Another problem with existing granular absorbent indicators is that the gradual color change from unreacted to reacted material makes it difficult to discern the location of the reaction front.

As shown in FIG. 2, the front of color indicator can move less than one-third the length of a granule filled canister from initial breakthrough to final exhaustion. This does not give the best possible resolution for consistently and accurately measuring the amount of unreacted adsorbent. It would be better if the color indicator front moved across the entire canister length, from initial breakthrough to final exhaustion.

Another problem is that many indicators used with granular $CO_2$ adsorbents revert back to their initial color after the end of a procedure (U.S. Pat. No. 7,476,641). This can happen in the calcium hydroxide system employing sodium hydroxide because the sodium hydroxide that is initially consumed in the reaction sequence—decreasing the pH and turning ethyl violet to purple—is slowly regenerated at the end of the reaction sequence, thereby increasing the pH and turning the ethyl violet back to clear. This makes it difficult to determine if partially used adsorbents beds have enough capacity to be used in another procedure.

In summary, there is a need for an adsorbent cartridge that gives a uniform and reproducible flow front with a sharply contrasting indicator that gives an accurate, objective and long lasting indication of the consumption state of the adsorbent within the cartridge. This invention addresses this need and others.

SUMMARY

The present invention is an adsorbent cartridge comprised of layers of adsorbent sheet with a color indicator system. The cartridge provides for a uniform flow front and the indicator displays the degree of consumption of the adsorbent in an objective, accurate and long lasting manner. This allows for maximum use of adsorbent in the cartridge before it is replaced. In one embodiment, windows (openings) are cut in an outermost layer of the adsorbent cartridge and color indicator is coated on an area on the layer beneath the outermost layer, so that it is visible through the window.

The absorbent cartridges described herein also allow for use of very little indicator dye compared to a granule bed (e.g., 1/100 to 1/100,000 less color indicator on a weight basis compared to a granule bed with a color indicator).

Accordingly, the present invention provides an adsorbent cartridge for removing gaseous contaminants, comprising layers of one or more self-supporting adsorbent sheets mechanically spaced to provide gas flow channels between the layers from one end of the cartridge to the other, wherein the cartridge further comprises a color indicator for visually indicating consumption of the adsorbent to an external observer, wherein at least one area of color indicator is visually exposed to an external observer while the cartridge is in use.

In some embodiments, the color indicator is visually exposed by windows cut into the side of the cartridge. In another embodiment, windows are cut in an outermost layer of the adsorbent cartridge. In some embodiments, a very thin color indicator layer with an area that is larger than the window area is placed between the window layer and the layer beneath the outermost layer, so that it is visible through the window.

In another embodiment, windows are cut in an outermost layer of the adsorbent cartridge and the window space is at least partially filled with a plug of indicating material that is the same areal dimensions as the plug.

In any embodiment using windows, a transparent layer may be placed over the outermost layer and its windows so that the indicator below the window can be seen without the gas in the cartridge escaping.

In another embodiment, stripes or other discrete geometric patterns can be coated onto the surface of the outer adsorbent layer of the cartridge.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1(d) depicts a cross-section view of an adsorption sheet of the present invention where the sheet is formed with adsorbent particles connected by polymer within.

FIG. 1(e) depicts a cross-section view of an adsorption sheet of the present invention where the sheet of FIG. 1(d) is surrounded by an outer membrane.

FIG. 1(f) depicts a cross-section view of an adsorption sheet of the present invention where adsorbent material is attached to an internal screen and outer membranes are attached to the adsorbent particles.

FIG. 1(g) depicts a cross-section view of an adsorption sheet of the present invention where outer membranes are attached to an internal screen and the interstices in the screen contain adsorbent material.

FIG. 1(q) depicts a detailed view of the adsorbent sheet illustrated in FIG. 1(p).

DETAILED DESCRIPTION

Figure 6:
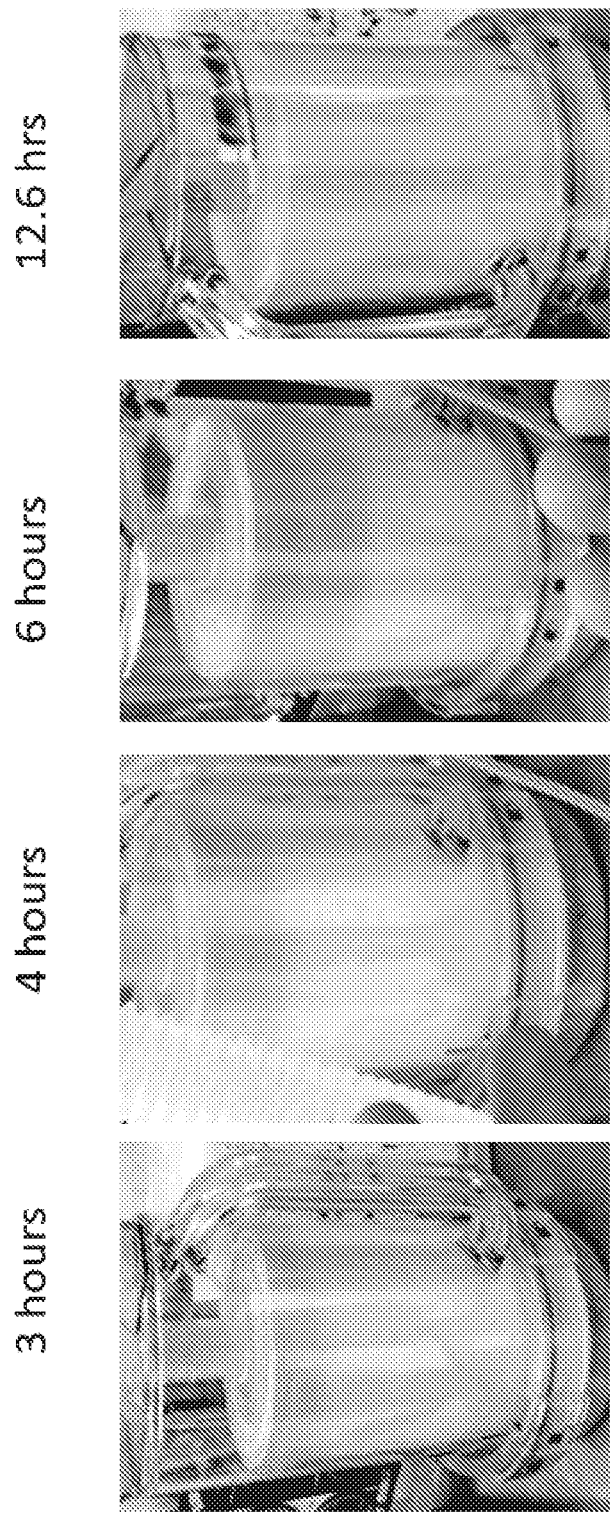
FIG. 6 depicts an adsorbent cartridge having a wound adsorbent sheet, to which has been applied ethyl violet indicator, after exposure to carbon dioxide after 3, 4, 6, and 12.6 hours.

The present invention is an adsorbent cartridge comprised of layers of adsorbent sheet with a color indicator system. The cartridge provides for uniform flow front (see FIG. 6) unlike a granule adsorbent front (see FIG. 2). Because the flow front is uniform, a color indicator as used in the present application can display the degree of consumption of the adsorbent in an objective, accurate and long lasting manner. This allows for maximum use of adsorbent in the cartridge before it is replaced.

Embodiments of the present application may be particularly useful for use in the administration of anesthesia, where it is desirable to consume as much of the $CO_2$ adsorbent as possible while not exposing the patient to excessive $CO_2$ levels that could be caused by gas channeling and premature breakthrough. Further, certain embodiments having discrete areas of color indicator allow the amount of indicator to be minimized, thereby increasing the safety of the instant adsorbent cartridge by minimizing any contamination from the indicator itself. The present invention may also be used as a means to reduce $CO_2$ and give visual indication of adsorbent consumption in other devices, such as underwater breathing apparatus.

As the mechanism for removing $CO_2$ from a gas or inhaled air is dependent on the particular material chosen, the use of the work 'adsorption' in this specification is meant to include adsorption, absorption, chemisorption and so forth.

Accordingly, the present application provides, inter alia, an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use.

In another embodiment, the present application provides an adsorbent cartridge for removing gaseous carbon dioxide contaminants, comprising a stack of self-supporting adsorbent sheets mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use.

In another embodiment, the present application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of the visually exposed areas of color indicator is equal to or less than the total surface area of the outermost layer of the cartridge.

In another embodiment, the present application provides an adsorbent cartridge for removing gaseous carbon dioxide contaminants, comprising a stack of self-supporting adsorbent sheets mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of the visually exposed areas of color indicator is equal to or less than the total surface area of the outermost layer of the cartridge.

In another embodiment, the present application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of all color indicator in the cartridge is equal to or less than the total surface area of the outermost layer of the cartridge; and wherein the total surface area of the visually exposed areas of color indicator is equal to or less than the total surface area of all color indicator in the cartridge.

In another embodiment, the present application provides an adsorbent cartridge for removing gaseous carbon dioxide contaminants, comprising a stack of self-supporting adsorbent sheets mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of all color indicator in the cartridge is equal to or less than the total surface area of the outermost layer of the cartridge; and wherein the total surface area of the visually exposed areas of color indicator is equal to or less than the total surface area of all color indicator in the cartridge.

As used herein, the "outermost layer" in the context of the spirally wound adsorbent cartridge refers to the final wound layer of the cartridge. The "outermost layer" in the context of the stacked adsorbent cartridge refers to the top or bottom sheet of the stack of adsorbent sheets.

As used herein, "self-supporting" adsorbent sheet means that the sheet does not require any external reinforcement for support after being wound or stacked.

As used herein, the "color indicator" refers to a dye that changes color when the absorbent is reacted. In the case of calcium hydroxide, this the color change occurs because of the decrease in pH due to the conversion of calcium hydroxide to calcium carbonate, as well as the short term consumption of sodium hydroxide. For example, for ethyl violet indicator, the pH changes to less than 10.3, causing the ethyl violet indictor to turn from clear to purple.

As used herein, "inner side of the adsorbent sheet" in the context of a spirally wound adsorbent cartridge means the side of adsorbent sheet that faces towards the core of wound roll.

As used herein, "the outer side of the adsorbent sheet" in the context of a spirally wound adsorbent cartridge means the side of the adsorbent sheet that faces away from the core of the wound roll.

As used herein, "total surface area of all color indicator in the cartridge" means the total surface area of all applied color indicator in the cartridge, whether applied directly to a layer of the cartridge, to an indicator layer, or to a plug of material comprising color indicator.

As used herein, "visually exposed areas of color indicator" means the areas of color indicator which are visible to an external observer because they are applied to the outermost layer of the cartridge or which are exposed due to windows cut in the outermost layer.

Embodiments below may be combined in any combination with the preceding embodiments.

In some embodiments, the cartridge is for use in an anesthesia breathing circuit. In some embodiments, the multiple layers are mechanically spaced by parallel, longitudinal ribs molded out of the sheet. As used herein, "parallel, longitudinal ribs" means that the ribs run parallel to the direction of air flow, thereby mechanically separating the sheet layers and providing gas flow channels. In some embodiments, the layers are mechanically spaced by additional spacer material. In some embodiments, the adsorbent material comprises calcium hydroxide. In some embodiments, the adsorbent material comprises lithium hydroxide.

In some embodiments, the adsorbent material comprises calcium hydroxide, sodium hydroxide, and potassium hydroxide. In some embodiments, the adsorbent material comprises calcium hydroxide and sodium hydroxide. In some embodiments, the adsorbent material further comprises sodium hydroxide, potassium hydroxide, calcium chloride, or lithium hydroxide. In some embodiments, the cartridge further comprising a transparent film covering the outermost layer of the cartridge. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the polymer comprises 0.25% to 10%, 0.25% to 9%, 0.25% to 8%, 0.25% to 7%, 0.25% to 6%, 0.25% to 5%, 0.25% to 4%, 0.25% to 3%, 0.25% to 2%, or 0.25% to 1% by weight of said sheet. In some embodiments, the polymer comprises 0.5% to 1%, 0.5% to 2%, 0.5% to 3%, 0.5% to 4%, 0.5% to 5%, 0.5% to 6%, 0.5% to 7%, 0.5% to 8%, 0.5% to 9%, 0.5% to 10%, 0.5% to 15%, or 0.5% to 20% by volume of the adsorbent material which is formed into the sheet. In some embodiments, the polymer is polyethylene. In some embodiments, the polymer is high-density polyethylene or ultra high molecular weight polyethylene. In some embodiments, the adsorbent sheet is made by a thermally induced phase separation process. In some embodiments, the polymer is a polyethylene binder. In some embodiments, the adsorbent sheet is made by a thermally induced phase separation process wherein the polymer is polyethylene that comprises 0.25% to 10%, 0.25% to 9%, 0.25% to 8%, 0.25% to 7%, 0.25% to 6%, 0.25% to 5%, 0.25% to 4%, 0.25% to 3%, 0.25% to 2%, or 0.25% to 1% by weight of said sheet.

In some embodiments, the ribbed adsorbent sheet is less than 0.10 inches, 0.09 inches, less than 0.08 inches, less than 0.07 inches, less than 0.06 inches, less than 0.05 inches, less than 0.04 inches, or less than 0.03 inches in thickness, including the ribs. In some embodiments, the thickness of the sheet, excluding the ribs is from 0.01 to 0.07 inches, or 0.01 to 0.08 inches. In some embodiments, the thickness of the ribs disposed on the sheet is from 0.01 to 0.04 inches. In some embodiments, the height of the ribs disposed on the sheet is from 0.005 to 0.05 inches. In some embodiments, the height of the ribs disposed on the sheet is from 0.005 to 0.08 inches.

The absorbent may be a single absorbent or a mixture of different adsorbents. In some embodiments, the adsorbent includes, but is not limited to, calcium hydroxide ($Ca(OH)_2$), lithium hydroxide (LiOH), calcium hydroxide mixed with a percentage of sodium and potassium hydroxide, other $CO_2$ adsorbents and mixtures thereof. In some embodiments, the adsorbent (e.g., calcium hydroxide) is mixed with other alkali metal hydroxides such as sodium hydroxide or potassium hydroxide. In some embodiments, the adsorbent particles form at least 75%, 80%, 85%, 90%, 95%, 96%, 97%, 99%, or 99.5% by weight of said sheet. In some embodiments, the adsorbent particles form at least 30%, 35%, 40%, 45%, 50%, 55%, 60%, 65%, 70%, or 75%, by volume of adsorbent material which is formed into the sheet.

The following sections detail specific embodiments of the present application. The embodiments in each individual paragraph can combined in any combination.

Discrete Areas of Indicator Applied to a Layer of the Cartridge

In some embodiments, the color indicator is applied to one or more layers of the cartridge solely on the outer side of the adsorbent sheet, wherein one or more discrete areas of color indicator are visible to external observer or are exposed visually to an external observer through windows cut into the outermost layer. In some embodiments, the cartridge is for use in an anesthesia breathing circuit. In some embodiments, the multiple layers are mechanically spaced by parallel, longitudinal ribs molded out of the sheet. In some embodiments, the layers are mechanically spaced by additional spacer material. In some embodiments, the adsorbent material comprises calcium hydroxide. In some embodiments, the adsorbent material comprises lithium hydroxide. In some embodiments, the adsorbent material further comprises sodium hydroxide, potassium hydroxide, calcium chloride, or lithium hydroxide. In some embodiments, the cartridge further comprises a transparent film covering the outermost layer of the cartridge. In some embodiments, the color indicator comprises ethyl violet, Titan yellow, Kenazol yellow, activated alumina with thymol blue, or o-cresolpthalein. In some embodiments, the color indicator comprises ethyl violet. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the adsorbent cartridge comprises $1/100$ to $1/100,000$ less color indicator on a weight basis compared to a granule bed with a color indicator.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein a color indicator for visually indicating consumption of the adsorbent to an external observer is applied to one or more layers of the cartridge solely on the outer side of the adsorbent sheet, wherein one or more discrete areas of color indicator are visible to external observer or are exposed visually to an external observer through windows cut into the outermost layer, wherein the total surface area of all color indicator in the cartridge is equal to or less than the total surface area of the outermost layer of the cartridge; and wherein the total surface area of the visually exposed areas of color indicator is equal to or less than the total surface area of all color indicator in the cartridge. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein an ethyl violet color indicator for visually indicating consumption of the adsorbent to an external observer is applied to one or more layers of the cartridge solely on the outer side of the adsorbent sheet, wherein one or more discrete areas of color indicator are visible to external observer or are exposed visually to an external observer through windows cut into the outermost layer, wherein the total surface area of all color indicator in the cartridge is equal to or less than the total surface area of the outermost layer of the cartridge; and wherein the total surface area of the visually exposed areas of color indicator is equal to or less than the total surface area of all color indicator in the cartridge. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein a color indicator for visually indicating consumption of the adsorbent to an external observer is applied to one or more layers of the cartridge solely on the outer side of the adsorbent sheet, wherein one or more discrete areas of color indicator are visible to external observer or are exposed visually to an external observer through windows cut into the outermost layer, wherein the total surface area of all color indicator in the cartridge is equal to or less than the total surface area of the outermost layer of the cartridge and wherein the total surface area of the visually exposed areas of color indicator is equal to or less than the total surface area of all color indicator in the cartridge. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide, wherein an ethyl violet color indicator for visually indicating consumption of the adsorbent to an external observer is applied to one or more layers of the cartridge solely on the outer side of the adsorbent sheet, wherein one or more discrete areas of color indicator are visible to external observer or are exposed visually to an external observer through windows cut into the outermost layer, wherein the total surface area of all color indicator in the cartridge is equal to or less than the total surface area of the outermost layer of the cartridge and wherein the total surface area of the visually exposed areas of color indicator is equal to or less than the total surface area of all color indicator in the cartridge. In some embodiments, the total surface area of visibly exposed areas of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer. In some embodiments, the total surface area of color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

Discrete Areas of Color Indicator Applied to the Outermost Layer of the Cartridge In some embodiments, the color indicator can be applied to one or more discrete areas of the outermost layer of the cartridge. The color indicator can be applied either directly to the outermost layer or as part of a coating containing another substances (e.g., a polymer binder). Hence, in some embodiments, each of the discrete areas of the color indicator are applied to the outermost layer of the cartridge. In some embodiments, the color indicator comprises ethyl violet, Titan yellow, Kenazol yellow, activated alumina with thymol blue, or o-cresolpthalein. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein color indicator for visually indicating consumption of the adsorbent to an external observer is applied to one or more discrete areas of the outermost layer of the cartridge, wherein the total surface area of the visually exposed areas of color indicator is equal to or less than the total surface area of the outermost layer of the cartridge. In some embodiments of the previous embodiment, the color indicator comprises ethyl violet, Titan yellow, Kenazol yellow, activated alumina with thymol blue, or o-cresolpthalein. In some embodiments of the previous embodiment, the color indicator comprises ethyl violet. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein ethyl violet color indicator for visually indicating consumption of the adsorbent to an external observer is applied to one or more discrete areas of the outermost layer of the cartridge, wherein the total surface area of the visually exposed areas of color indicator is equal to or less than the total surface area of the outermost layer of the cartridge. In some embodiments of the previous embodiment, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide, wherein color indicator for visually indicating consumption of the adsorbent to an external observer is applied to one or more discrete areas of the outermost layer of the cartridge, wherein the total surface area of the visually exposed areas of color indicator is equal to or less than the total surface area of the outermost layer of the cartridge. In some embodiments of the previous embodiment, the color indicator comprises ethyl violet, Titan yellow, Kenazol yellow, activated alumina with thymol blue, or o-cresolpthalein. In some embodiments of the previous embodiment, the color indicator comprises ethyl violet. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide, wherein ethyl violet color indicator for visually indicating consumption of the adsorbent to an external observer is applied to one or more discrete areas of the outermost layer of the cartridge, wherein the total surface area of the visually exposed areas of color indicator is equal to or less than the total surface area of the outermost layer of the cartridge. In some embodiments of the previous embodiment, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments of any of the previous embodiments of this paragraph, the cartridge further comprising a transparent film covering the outermost layer of the cartridge. In some embodiments of any of the previous embodiments of this paragraph, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

Color Indicator Applied to Layer Beneath the Outermost Layer of the Cartridge

Instead of applying the color indicator to the outermost layer, windows can be cut into the outermost layer of the adsorbent cartridge. Color indicator can then be applied directly or as a coating (e.g., with another material like a binder or polymer) to the layer beneath the outermost layer of the cartridge. In the case of spirally wound cartridge, this would be the layer (or wrap) of the adsorbent sheet under the outermost layer. In the case of the stacked cartridge, this would be the adsorbent sheet immediately under the outermost adsorbent sheet in the stack. The size of the area(s) of color indicator may be larger or smaller than the size of the window, but should be viewable through the window.

Accordingly, in some embodiments, in some embodiments, the color indicator can be applied to one or more discrete areas of the layer beneath the outermost layer of the cartridge. The color indicator can be applied either directly to the layer beneath the outermost layer or as part of a coating containing another substances (e.g., a polymer binder). Hence, in some embodiments, each of the discrete areas of the color indicator are applied to the layer beneath the outermost layer of the cartridge. In some embodiments, the color indicator comprises ethyl violet, Titan yellow, Kenazol yellow, activated alumina with thymol blue, or o-cresolpthalein. In some embodiments, the color indicator is ethyl violet. In some embodiments, the cartridge further comprises a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein color indicator for visually indicating consumption of the adsorbent to an external observer is applied to one or more discrete areas of the layer beneath the outermost layer of the cartridge and the one or more discrete areas of the color indicator are exposed visually to the external observer by windows cut in the outermost layer of the cartridge, wherein the total surface area of all areas of color indicator is equal to or less than the total surface area of the outermost layer of the cartridge. In some embodiments of the previous embodiment, the color indicator comprises ethyl violet, Titan yellow, Kenazol yellow, activated alumina with thymol blue, or o-cresolpthalein. In some embodiments of the previous embodiment, the color indicator comprises ethyl violet. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide, wherein ethyl violet color indicator for visually indicating consumption of the adsorbent to an external observer is applied to one or more discrete areas of the layer beneath the outermost layer of the cartridge and the one or more discrete areas of the color indicator are exposed visually to the external observer by windows cut in the outermost layer of the cartridge, wherein the total surface area of all areas of color indicator is equal to or less than the total surface area of the outermost layer of the cartridge. In some embodiments of the previous embodiment, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide, wherein color indicator for visually indicating consumption of the adsorbent to an external observer is applied to one or more discrete areas of the layer beneath the outermost layer of the cartridge and the one or more discrete areas of the color indicator are exposed visually to the external observer by windows cut in the outermost layer of the cartridge, wherein the total surface area of all areas of color indicator is equal to or less than the total surface area of the outermost layer of the cartridge. In some embodiments of the previous embodiment, the color indicator comprises ethyl violet, Titan yellow, Kenazol yellow, activated alumina with thymol blue, or o-cresolpthalein. In some embodiments of the previous embodiment, the color indicator comprises ethyl violet. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the present application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide, wherein ethyl violet color indicator for visually indicating consumption of the adsorbent to an external observer is applied to one or more discrete areas of the layer beneath the outermost layer of the cartridge and the one or more discrete areas of the color indicator are exposed visually to the external observer by windows cut in the outermost layer of the cartridge, wherein the total surface area of all areas of color indicator is equal to or less than the total surface area of the outermost layer of the cartridge. In some embodiments of the previous embodiment, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments of any of the previous embodiments of this paragraph, the cartridge further comprising a transparent film covering the outermost layer of the cartridge. In some embodiments of any of the previous embodiments of this paragraph, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the cartridge can be used in conjunction with a flow cone for improving uniformity of flow, which is placed at the gas inlet and/or outlet end of the cartridge. For example, appropriate flow cones are described in U.S. Pat. No. 7,326,280, which is incorporated herein by reference in its entirety.

Use of an Indicator Layer

In another configuration, windows can be cut into the outermost layer of the adsorbent cartridge as above. In some embodiments, a single window may be cut, while in other embodiments, multiple windows can be cut. However, instead of applying the color indicator to a particular layer of the cartridge itself, an indicator layer comprising a color indicator can then be sandwiched between the outermost layer and a layer immediately beneath the outermost layer. The indicator layer should be thin to minimize any bulging of the adsorbent cartridge. The indicator layer may have the color indicator applied to part or the entire surface of the indicator surface, on one side or both sides of the indicator layer. In some embodiments, the color indicator may be patterned in discrete areas of the indicator layer rather than in a continuous area. If coated on one side, the color indicator should be positioned on the side facing the window so that the color change can be viewed through the window by an external observer. The indicator layer may be a film or other thin material coated with the color indicator. If using discrete areas of color indicator on the indicator layer, the size of the discrete area of color indicator may be larger or smaller than the size of the window, but should be viewable through the window. In some embodiments, a single indicator layer may be used, but positioned so the area of color indicator is visible through the window(s) in the outermost layer. In some embodiments, separate thin indicator layers (patches) can be used for each window cut into the outermost layer.

Accordingly, in some embodiments, the color indicator comprises part of an indicator layer sandwiched between the outermost layer and the layer beneath the outermost layer of the cartridge, wherein each discrete area of color indicator is exposed by a window cut in the outermost layer of the cartridge. In some embodiments, the indicator is 30 mils or less in thickness. In some embodiments, the indicator layer is 20 mils or less in thickness. In some embodiments, the indicator layer is 10 mils or less in thickness. In some embodiments, the indicator layer is formed from a mixture comprising calcium hydroxide, sodium hydroxide, and a polymer, to which the color indicator has been applied. In some embodiments, the color indicator is ethyl violet. In some embodiments, the color indicator comprises Titan yellow, Kenazol yellow, activated alumina with thymol blue, or o-cresolpthalein. In some embodiments, the adsorbent material comprises lithium hydroxide. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

The cartridge can have a single window and a single indicator layer comprising an area of color indicator is positioned so that the area of color is positioned so that the area of color indicator is viewable through the window. Accordingly, in some embodiments, the cartridge has a single window, wherein the indicator layer has a single discrete area of the color indicator positioned to center on the window in the outermost layer of the cartridge. In some embodiments, the indicator layer is formed from a mixture of calcium hydroxide, sodium hydroxide, and a polymer, to which the discrete area of color indicator has been applied. In some embodiments, the color indicator is ethyl violet. In some embodiments, the adsorbent material comprises lithium hydroxide. In some embodiments, the cartridge further comprising a transparent film covering the outermost layer of the cartridge. In some embodiments, the color indicator is applied only to part of the indicator layer. In some embodiments, the color indicator is applied to the entire indicator layer (e.g, the indicator layer is used as patch under the window). In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In a further embodiment, the indicator layer may be patterned with discrete areas of color indicator rather than being completely coated with color indicator. If coated on one side of the indicator layer, the color indicator should be positioned on the side facing the window so that the color change can be viewed through the window by an external observer. The indicator layer is then positioned such that the areas of color indicator can be viewed through the windows cut in the outermost layer of the adsorbent.

Hence, in some embodiments, the cartridge has multiple windows, wherein the indicator layer has multiple discrete areas of the color indicator positioned to center on the windows in the outermost layer of the cartridge. In some embodiments, the indicator layer is formed from a mixture of calcium hydroxide, sodium hydroxide, and a polymer, to which the discrete areas of color indicator have been applied. In some embodiments, the color indicator is ethyl violet. In some embodiments, the adsorbent material comprises lithium hydroxide. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In another embodiment, the indicator layer can be a strip which to which the color indicator is applied. The strip can be placed longitudinally under the outermost layer of the adsorbent cartridge. One or more windows can then be cut into the outermost layer above the strip, allowing discrete areas of color indicator to be viewed through the window(s).

In another embodiment, the indicator layer can be a film or strip positioned on the outermost layer of the cartridge over a window cut into the outermost layer of the cartridge.

Accordingly, in some embodiments, the cartridge has multiple windows, wherein the indicator layer is a strip positioned such that the area exposed by each window is covered by said strip, thereby exposing the color indicator to said external observer. In some embodiments, the strip is formed from a mixture of calcium hydroxide, sodium hydroxide, and a polymer, to which the color indicator has been applied. In some embodiments, the color indicator is ethyl violet. In some embodiments, the adsorbent material comprises lithium hydroxide.

In yet another embodiment, separate thin indicator layers (patches) can be used for each window cut into the outermost layer, rather than a single strip or indicator layer. The color indicator can be applied to each patch and then positioned beneath each window, such that the area of color indicator is viewable through the window cut in the outermost layer.

Accordingly, in some embodiments, the cartridge has multiple windows, wherein a separate indicator layer is utilized for each window. In some embodiments, the indicator layer is formed from a mixture of calcium hydroxide, sodium hydroxide, and a polymer, to which the discrete areas of color indicator have been applied. In some embodiments, the color indicator is ethyl violet. In some embodiments, the adsorbent material comprises lithium hydroxide. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising lithium hydroxide; wherein the color indicator for visually indicating consumption of the adsorbent to an external observer is applied to an indicator layer sandwiched between the outermost layer and the layer beneath the outermost layer, wherein one or more discrete areas of color indicator are exposed visually to external observer through windows cut into the outermost layer; wherein the total surface area of all color indicator in the cartridge is equal to or less than the total surface area of the outermost layer of the cartridge. In some embodiments of the previous embodiment, the indicator layer is a sheet formed from a mixture comprising calcium hydroxide, sodium hydroxide, and a polymer, to which the color indicator is applied, wherein the color indicator is ethyl violet. In some embodiments of either of the previous two embodiments, the indicator layer is 10 mils or less in thickness (or alternatively, 20 mils or less in thickness, or alternatively, 30 mils or less). In some of any of the previous three embodiments, the cartridge has a single window in the outermost layer of the cartridge, wherein the indicator layer partially or completely covers the layer beneath the outermost layer of the cartridge, but wherein the indicator layer has a single discrete area of the color indicator positioned to center on the window in the outermost layer of the cartridge. In some embodiments of any of the previous three embodiments, the cartridge has multiple windows, wherein the indicator layer partially or completely covers the layer beneath the outermost layer of the cartridge, but the indicator layer has multiple discrete areas of the color indicator positioned to center on the windows in the outermost layer of the cartridge. In some embodiments of any of the previous three embodiments, the cartridge has one or more windows, the indicator layer partially or completely covers the layer beneath the outermost layer of the cartridge, and the color indicator is applied to the entire indicator layer, wherein the only areas of color indicator visible to the external observer are through each window. In some embodiments of any of the previous three embodiments, the cartridge has multiple windows, wherein the indicator layer is a strip positioned such that the area exposed by each window is covered by said strip, thereby exposing the color indicator to said external observer. In some embodiments of any of the previous three embodiments, the cartridge has multiple windows, wherein a separate indicator layer is utilized for each window. In some embodiments of any of the previous embodiments of this paragraph, the cartridge further comprising a transparent film covering the outermost layer of the cartridge. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments of any of the previous embodiments of this paragraph, the indicator layer completely covers the layer beneath the outermost layer of the cartridge. In some embodiments of any of the previous embodiments of this paragraph, the indicator layer partially covers the layer beneath the outermost layer of the cartridge. In some embodiments, the cartridge further comprising a transparent film covering the outermost layer of the cartridge. In some embodiments, each discrete area of color indicator is 0.05% to 50% of the surface area of the outermost layer. In some embodiments, the total surface area of all color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide; wherein the color indicator for visually indicating consumption of the adsorbent to an external observer is applied to an indicator layer sandwiched between the outermost layer and the layer beneath the outermost layer, wherein one or more discrete areas of color indicator are exposed visually to external observer through windows cut into the outermost layer; wherein the total surface area of all color indicator in the cartridge is equal to or less than the total surface area of the outermost layer of the cartridge. In some embodiments of the previous embodiment, the indicator layer is a sheet formed from a mixture comprising calcium hydroxide, sodium hydroxide, and a polymer, to which the color indicator is applied, wherein the color indicator is ethyl violet. In some embodiments of the previous embodiment, the indicator layer is a sheet formed from a mixture comprising calcium hydroxide, sodium hydroxide, and a polymer, to which the color indicator is applied, wherein the color indicator is ethyl violet. In some embodiments of either of the previous two embodiments, the indicator layer is 10 mils or less in thickness (or alternatively, 20 mils or less in thickness, or alternatively, 30 mils or less in thickness). In some of any of the previous three embodiments, the cartridge has a single window in the outermost layer of the cartridge, wherein the indicator layer partially or completely covers the layer beneath the outermost layer of the cartridge, but wherein the indicator layer has a single discrete area of the color indicator positioned to center on the window in the outermost layer of the cartridge. In some embodiments of any of the previous three embodiments, the cartridge has multiple windows, wherein the indicator layer partially or completely covers the layer beneath the outermost layer of the cartridge, but the indicator layer has multiple discrete areas of the color indicator positioned to center on the windows in the outermost layer of the cartridge. In some embodiments of any of the previous three embodiments, the cartridge has multiple windows, wherein the indicator layer is a strip positioned such that the area exposed by each window is covered by said strip, thereby exposing the color indicator to said external observer. In some embodiments of any of the previous three embodiments, the cartridge has one or more windows, the indicator layer partially or completely covers the layer beneath the outermost layer of the cartridge, and the color indicator is applied to the entire indicator layer, wherein the only areas of color indicator visible to the external observer are those viewed through each window. In some embodiments of any of the previous three embodiments, the cartridge has multiple windows, wherein a separate indicator layer is utilized for each window. In any of the previous embodiments of this paragraph, the cartridge further comprising a transparent film covering the outermost layer of the cartridge. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments of any of the previous embodiments of this paragraph, the indicator layer completely covers the layer beneath the outermost layer of the cartridge. In some embodiments of any of the previous embodiments of this paragraph, the indicator layer partially covers the layer beneath the outermost layer of the cartridge. In some embodiments, the cartridge further comprising a transparent film covering the outermost layer of the cartridge. In some embodiments, each discrete area of color indicator is 0.05% to 50% of the surface area of the outermost layer. In some embodiments, the total surface area of all color indicator in the cartridge is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

Use of a Plug of Indicator

In some embodiments, the cartridge has one or more windows cut out of the outermost layer of the cartridge, wherein visibly exposed discrete areas of color indicator are formed by a plug of material comprising the color indicator which at least partially fills each window. In some embodiments of the previous embodiments, the plug has the same length and width dimensions as each window. In some embodiments, the indicator layer is formed from a mixture of calcium hydroxide, sodium hydroxide, and a polymer, to which the color indicator has been applied. In some embodiments, the color indicator is ethyl violet. In some embodiments, the color indicator comprises Titan yellow, Kenazol yellow, activated alumina with thymol blue, or o-cresolpthalein. In some embodiments, the adsorbent material comprises lithium hydroxide. In some embodiments, the plug is 4 to 100 mils in thickness. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising lithium hydroxide; wherein the cartridge has one or more windows cut out of the outermost layer of the cartridge, each window being at least partially filled with a plug of material comprising a color indicator for visually indicating consumption of the adsorbent to an external observer. In some embodiments of the previous embodiment, the plug is formed from a mixture comprising calcium hydroxide, sodium hydroxide, and a polymer, to which the color indicator is applied, wherein the color indicator is ethyl violet. In some embodiments of either of the previous two embodiments, the plug is 4 to 100 mils in thickness. In some embodiments of any of the previous embodiments of this paragraph, the cartridge further comprising a transparent film covering the outermost layer of the cartridge. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

In some embodiments, the application provides an adsorbent cartridge for removing gaseous carbon dioxide contaminants for use in an anesthesia breathing circuit, comprising an adsorbent sheet wound into a roll to form multiple layers which are mechanically spaced by parallel, longitudinal ribs molded out of the sheet to provide gas flow channels between the layers, wherein the sheet is formed from a mixture comprising polymer and an adsorbent material comprising calcium hydroxide; wherein the cartridge has one or more windows cut out of the outermost layer of the cartridge, each window being at least partially filled with a plug of material comprising a color indicator for visually indicating consumption of the adsorbent to an external observer. In some embodiments of the previous embodiment, the plug is formed from a mixture comprising calcium hydroxide, sodium hydroxide, and a polymer, to which the color indicator is applied, wherein the color indicator is ethyl violet. In some embodiments of either of the previous two embodiments, the plug is 4 to 100 mils in thickness. In some embodiments of any of the previous embodiments of this paragraph, the cartridge further comprising a transparent film covering the outermost layer of the cartridge. In some embodiments of any of the previous embodiments of this paragraph, at least one of the discrete areas of color indicator is positioned at the end of the cartridge from which the gas exits. In some embodiments of any of the previous embodiments of this paragraph, the discrete areas of color indicator are positioned at various points in the direction of gas flow so consumption of the adsorbent material can be assessed. In some embodiments, the cartridge further comprising a transparent film covering the outermost layer of the cartridge. In some embodiments, each discrete area of color indicator is 0.05% to 50% of the surface area of the outermost layer. In some embodiments, each discrete area of color indicator is 0.05% to 40%, 0.05% to 30%, 0.05% to 25%, 0.05% to 20%, 0.05% to 15%, 0.05% to 10%, 0.05% to 5%, 0.05% to 4%, 0.05% to 3%, 0.05% to 2%, 0.05% to 1%, or 0.5% to 5% of the surface area of the outermost layer.

Formation of Adsorbent Sheets and Cartridges

In certain embodiments, a wound adsorbent may be made using an adsorbent sheet wrapped with alternating layers of spacer material. Other forms include, but are not limited to wound extruded adsorbent sheets where ribs are molded directly into the adsorbent, thereby creating gas flow channels. In another embodiment adsorbent sheets can be stacked on top of each other. Gas flow channels by mechanically spacing the adsorbent sheets with alternating layers of spacer material, or by molding ribs directly into the adsorbent sheet. The properties of the adsorbent sheet are such that no other supporting or containment fabric or material is needed to maintain structural integrity or rigidity. Embodiments of such forms are described in U.S. Pat. Nos. 5,964,221, 7,326,280, 7,329,307, 8,413,655 and 8,685,153 all incorporated by reference in their entireties.

Figure 1B:
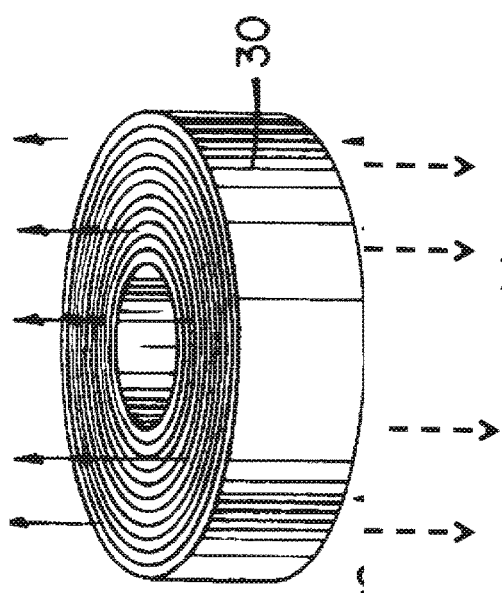
FIG. 1(b) depicts a cross-section top view of the adsorption canister of FIG. 1(a) where the sheets inside the canister have a spiral configuration.
Figure 1C:
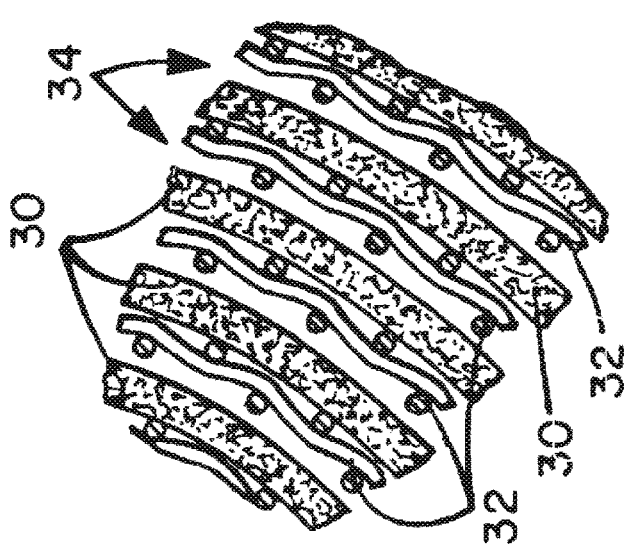
FIG. 1(c) depicts an enlargement of the circular area of the cross-section shown in FIG. 1(b) showing the sheets separated by a separating means.
Figure 1A:
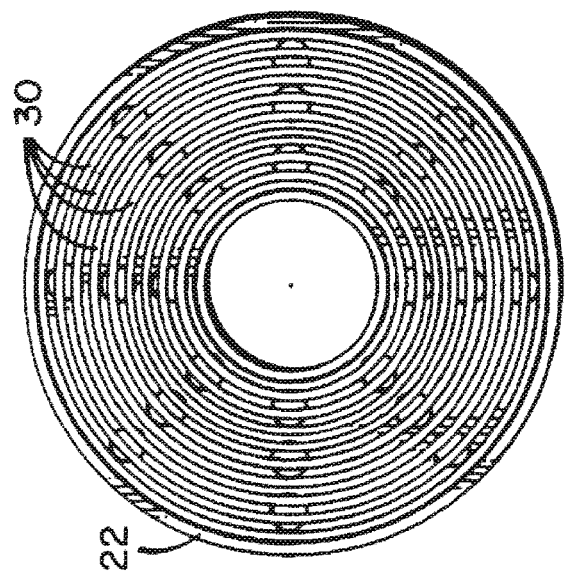
FIG. 1(a) depicts a three-quarter perspective view of an adsorption cartridge of the present invention where the cartridge is cylindrical and the sheets are spiral.

In some embodiments, the sheets are wound into a cylinder but the cartridge may also be of other geometries. In the wound embodiments, the sheet 30 is spiraled (i.e., arranged in a continuous helix or as separate rings or helixes arranged concentrically) as shown as illustrated in FIG. 1(a). Air flow through the cartridge can be from both directions (top to bottom, or bottom to top) and is parallel to the spiraled adsorbent sheet surfaces. FIG. 1(b) shows a top view of cylindrical cartridge of FIG. 1(a) with adsorbent sheet 30 arranged in a "spiral" configuration within a canister 22 where the sheet is wrapped around the center. FIG. 1(c) shows separating screens 32 positioned between the spirally positioned sheets 30 that allow gas flow through the space 34 between the sheets 30.

In some embodiments, the sheets are stacked into a cube or rectangular shape (90 degree corners on all sides but length, width and depth may or may not be identical). In some embodiments, the adsorbent surfaces are planar. The term "planar" used to describe surfaces means that the adsorbent surfaces are substantially without curvature (e.g., the surfaces are not rolled). A sealing material (foam or rigid) may be used to seal two or more sides of the cube or rectangle, leaving two open end faces (to allow for air flow), two outer surfaces formed by the adsorbent sheets, and two foam surfaces.

In some embodiments, each adsorbent surface comprises the same type of adsorbent. In other embodiments, each adsorbent surface is independently selected from various adsorbents.

In some embodiments, the adsorbent material used in the adsorbent surfaces is calcium hydroxide or lithium hydroxide. Further description of LiOH adsorbent sheets can be found in, for example, Hrycak et al. in U.S. Pat. Nos. 7,329,307 and 7,326,280, each of which is incorporated herein by reference in its entirety. Further description of $Ca(OH)_2$ adsorbent sheets and other types of adsorbent sheets can be found in, for example, in McKenna, U.S. Pat. No. 5,964,221, which is incorporated herein by reference in its entirety.

In one embodiment shown in FIG. 1(d), sheet 30 is formed of an adsorbent filled expanded porous polymer (e.g., PTFE) sheet having a microstructure of nodes 40 interconnected with fibrils 41 wherein adsorbent material 39 is present in the voids of the polymer structure as taught by U.S. Pat. No. 4,985,296 issued to Mortimer, Jr., incorporated herein by reference in its entirety. This sheet is water repellent, but air-permeable. Ideally, particles 39 are packed in a multi-modal (e.g., bi-modal or tri-modal) manner, with particles of different sizes interspersed around one another to fill as much of the available void space between particles as is possible so as to maximize the amount of active material contained in the sheet. This technique also allows more than one type of adsorbent particle to be filled into a single sheet. In some embodiments, the adsorbent sheet is made using a thermally induced phase separated process.

In some embodiments, the sheet can be made using PTFE. By using filled porous expanded polytetrafluoroethylene (PTFE) as sheet 30 (or other thermally induced phase separated polymer), a number of additional advantages are further imparted. Expanded PTFE is a non-linting, non-outgassing inert material that effectively reduces dusting of adsorbent material during manufacturing and during the life of the filter. Additionally, processing advantages of this material include the ability to make a relatively thin material that can be produced in a wide sheet and then cut (or cut and pleated) into desired configurations.

The properties of $CO_2$ adsorbent filled polymer sheet are such that no other supporting fabric or material is needed to maintain structural integrity. In fact, not only can the adsorbent sheet withstand flexing, pleating and mechanical vibration under dry conditions, when PTFE is used, the hydrophobicity of the PTFE offers this structural durability even while subjected to direct liquid water contact. Another embodiment of sheet 30 is shown in FIG. 1(e), where filled polymer sheet 30 is encapsulated between two hydrophobic gas-permeable membranes 42. These outer membranes 42 add extra protection to ensure that adsorption material 40 is contained within sheet 30 while preventing water from reaching the adsorbent contained in the sheet. Membranes 42 must have a high degree of filtration efficiency to prevent adsorbent particles from escaping into the breathing atmosphere. These membranes 42 preferably comprise porous expanded polytetrafluoroethylene (PTFE), because it is hydrophobic and offers high particulate filtration efficiency.

A third embodiment of the sheet is shown in cut-away FIG. 1(f), where an internal screen 43 is encapsulated by adsorbent material 39 that is surrounded by two hydrophobic gas-permeable membranes 42.

A fourth embodiment of the sheet 30 is shown in FIG. 1(g) where an internal screen 44 is attached to two hydrophobic gas-permeable membranes 42 and adsorbent material 39 is positioned in the voids between screen members 44.

Figure 1J:
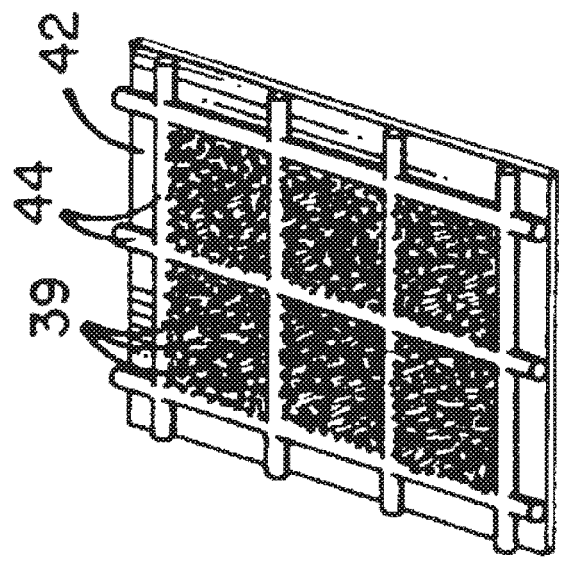
FIGS. 1(h) through 1(k) depict three-quarter elevation views of a method for forming the sheet of FIG. 1(g).
Figure 1I:
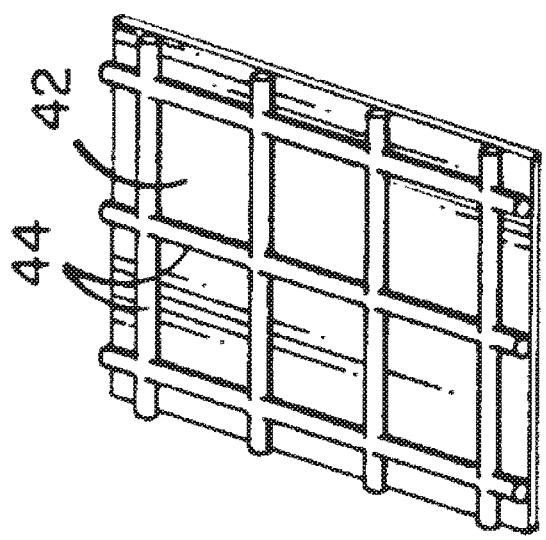
Figure 1K:
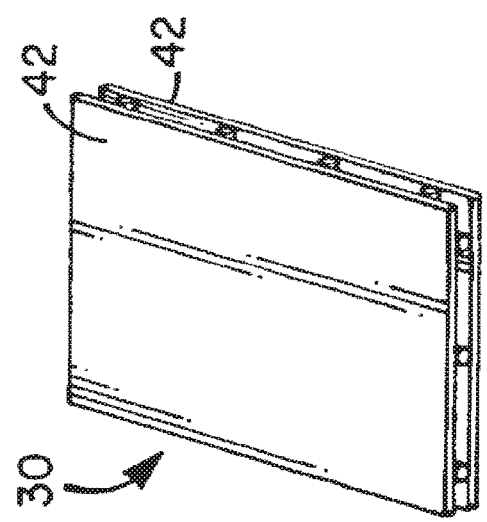
Figure 1H:
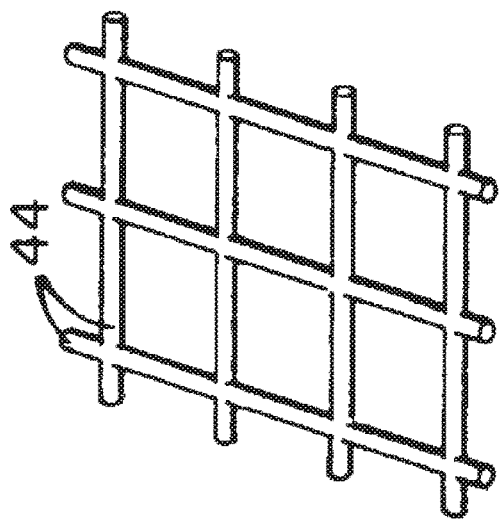

FIGS. 1(h) thorough 1(k) illustrate a method for making sheet 30 of FIG. 1(g) having an internal screen 44, adsorbent material 39, and outer membranes 42. FIG. 1(h) depicts internal screen 44. Next, in FIG. 1(i), internal screen 44 is attached to a membrane 42 by a lamination process. Subsequently, in FIG. 1(j), adsorbent material 39 is added into the open cells of internal screen 44. Afterwards, in FIG. 1(k), a second membrane 42 is laminated to the top of the internal screen 44, thereby encapsulating adsorbent material 40 within.

Figure 1L:
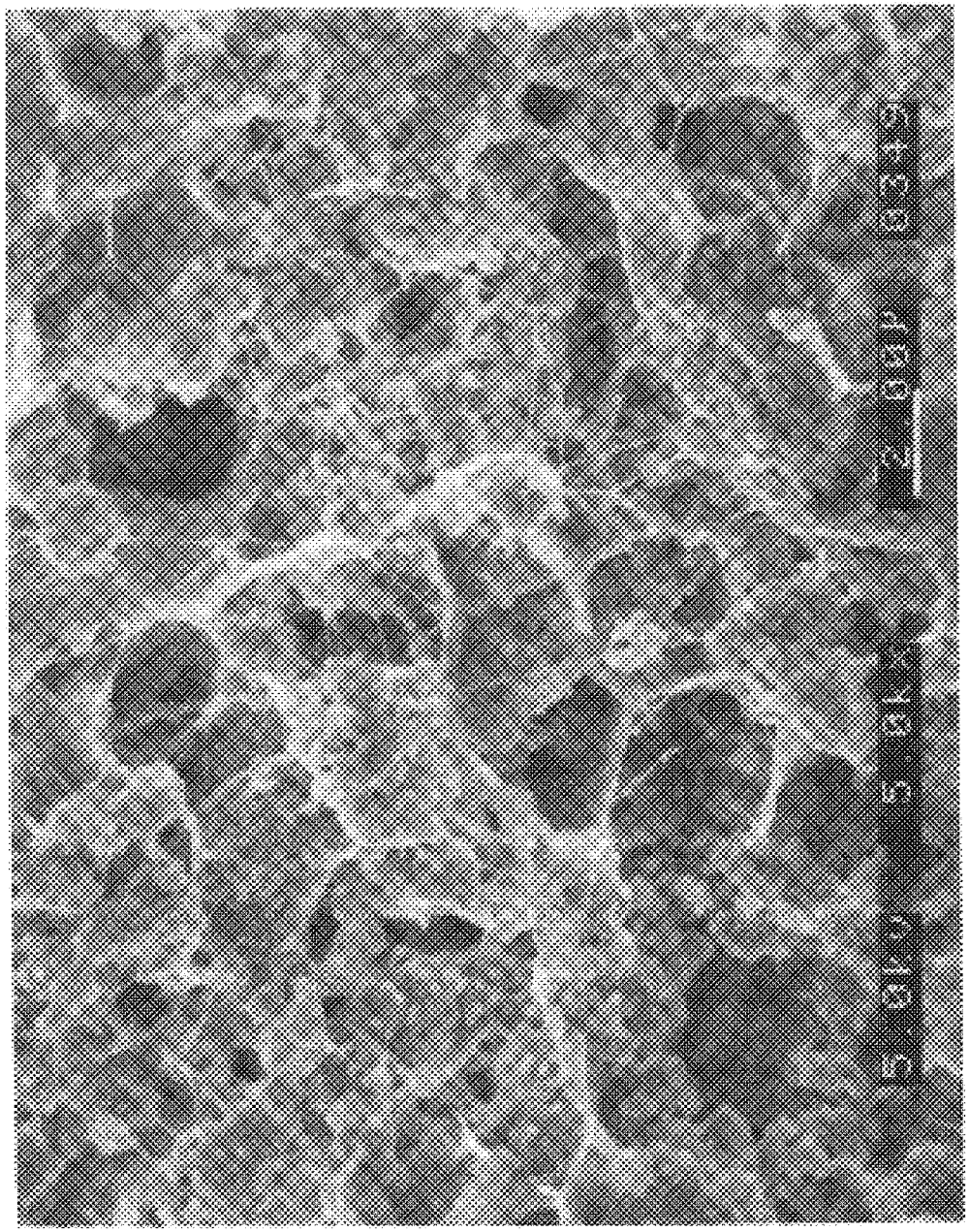
FIG. 1(l) depicts a scanning electron micrograph (SEM), enlarged 5,000 times, of a cross section of an adsorbent sheet of the present invention were the adsorbent powder is formed into a microporous sheet by thermally induced phase separation of polyethylene.
Figure 1M:
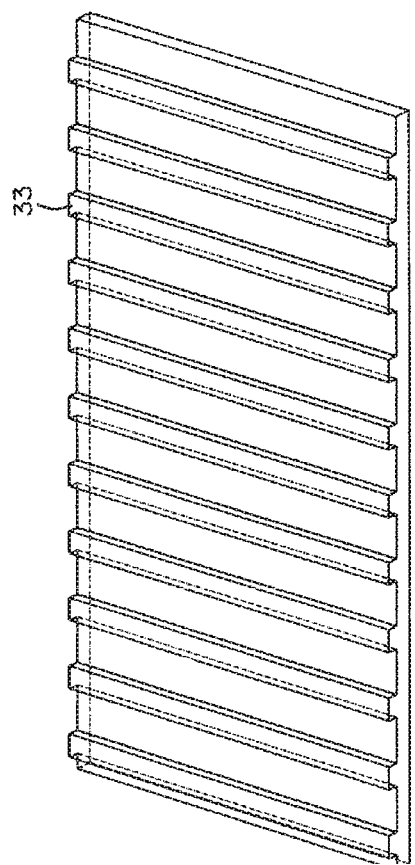
FIG. 1(m) depicts a three-quarter top elevation view of an adsorbent sheet for use in the present invention, in which separating ribs have been molded on one side of the sheet out of the adsorbent itself.
Figure 1N:
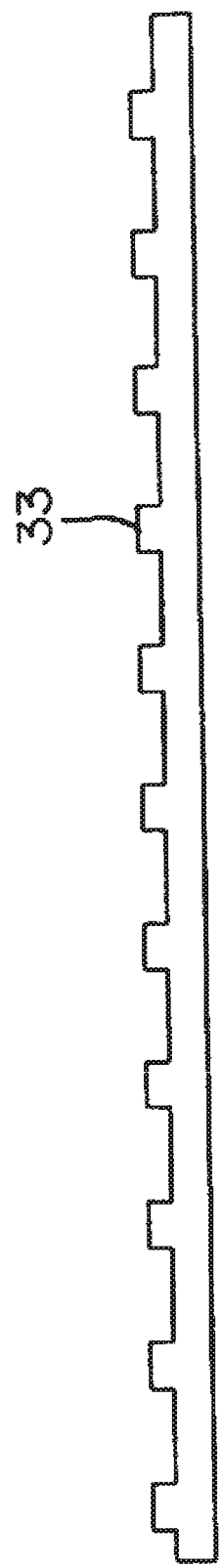
FIG. 1(n) depicts a cross-section view of the adsorbent sheet shown in FIG. 1(m).
Figure 1O:
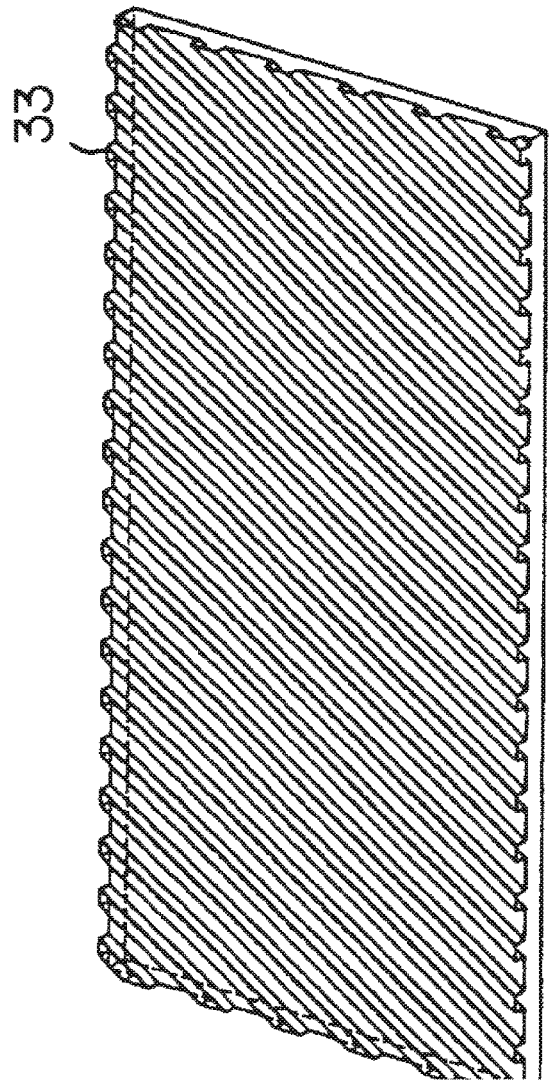
FIG. 1(o) depicts a three-quarter top elevation view of another embodiment of an adsorbent sheet for use in the present invention, in which separating ribs have been molded in an angular fashion on one side of the adsorbent sheet.
Figure 1P:
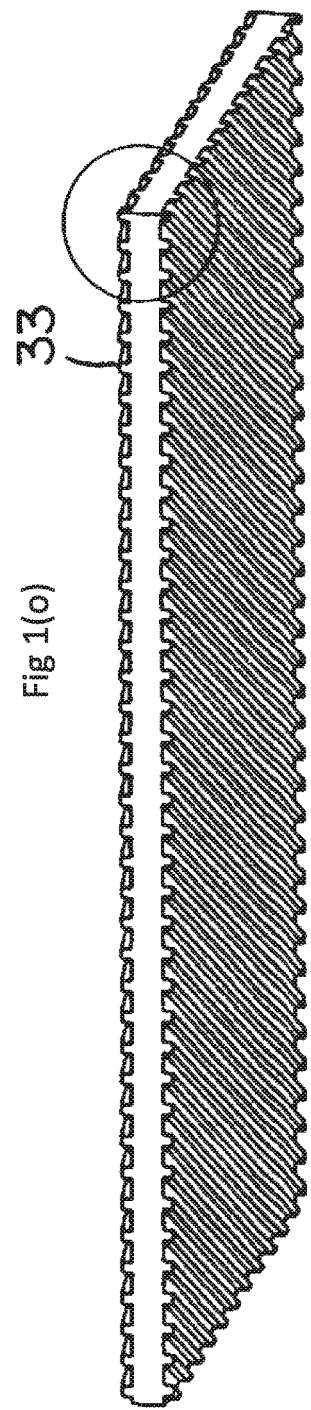
FIG. 1(p) depicts a three-quarter side elevation view of still another embodiment of an adsorbent sheet for use in the present invention, in which separating ribs have been molded in an angular fashion on both sides of the adsorbent sheet.

FIG. 1(l) is a scanning electron micrograph of another embodiment of sheet 30 used in the cartridges described herein. This structure is produced by way of thermally induced phase separation, such as in the following manner.

A water repellent polymer, such as ultra high molecular weight polyethylene, is combined with a gas adsorbent material, such as calcium hydroxide powder. This combination may be accomplished by combining the two materials together in an extruder. By conveying this mixture through the extruder and mixing with a lubricant, such as mineral oil, the polymer dissolves in the lubricant and become uniformly mixed with the adsorbent and lubricant. This mixture can then be extruded into a composite sheet or other shape.

The composite sheet may be calendared to further flatten the sheet if desired. The lubricant may then be extracted out of the resulting sheet using a solvent, such as hexane. The solvent may then be removed, such as through use of a dry nitrogen purge.

The resulting structure is highly micro-porous, allowing for the diffusion of $CO_2$ or other gases, and yet is able to be produced with very high adsorbent powder loadings per unit volume. Additionally, if a very strong polymer, such as Ultra High Molecular Weight Polyethylene is used, a very small amount of polymer is required to make the sheet structurally stable, which allows for even higher adsorbent loadings per unit volume. While typical powder loadings for this type of manufacturing process are on the order of 50 to 60% filler powder after process oil extraction, loadings well above 60% may be possible. In some embodiments, adsorbent loading is greater or equal to about 90% by weight. In some embodiments, adsorbent loading is greater or equal to about 97%. Additionally, in some embodiments, the material is molded into any desired shape, and thus, the separating means may be accomplished by molding separating ribs onto the surface of the sheet.

Various embodiments of this molded structure are illustrated in FIGS. 1(m) through 1(q). By molding the separating elements 33 (or "ribs") directly out of adsorbent material, not only is the adsorbent cartridge easier to produce, but, because of its self-separating properties, the total amount of adsorbent in the filter can be increased by 10 to 30 percent.

Figure 3A:
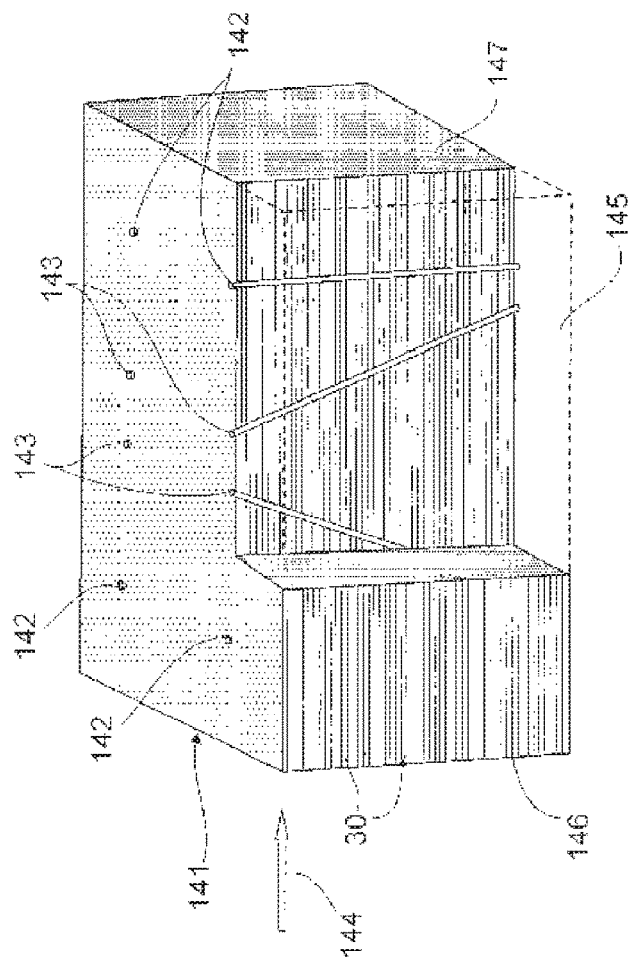
FIG. 3a depicts an adsorbent cartridge having ribs molded from the adsorbent sheet which provide flow channels when stacked.
Figure 3:
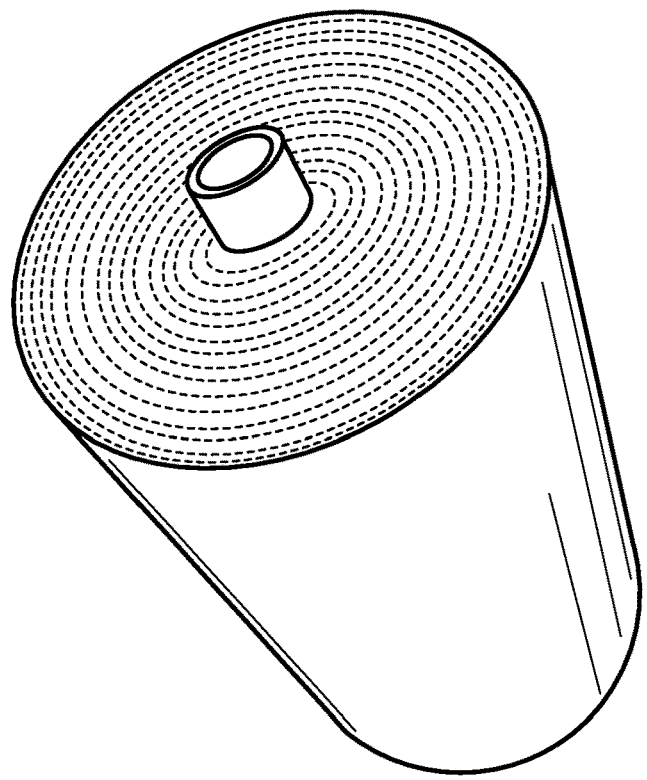
FIG. 3 depicts an adsorbent cartridge having ribs molded from the adsorbent sheet which provide gas flow channels when wound.

In some embodiments, the cartridge is formed from a self-supporting adsorbent sheet wound into a roll to form multiple layers mechanically spaced to provide gas flow channels between the layers from one end of the cartridge to the other (e.g., FIG. 3). For example, in some embodiments, the cartridge can be formed as in U.S. Pat. No. 5,964,221, which is incorporated herein by reference in its entirety.

In another embodiment, the cartridge is formed by a stack of self-supporting adsorbent sheets mechanically spaced to provide gas flow channels between the layers from one end of the cartridge to the other (e.g., FIG. 3a). For example, the cartridge can be formed as described in U.S. Pat. No. 8,685,153, which is incorporated herein by reference in its entirety. FIG. 3a shows an embodiment of a self-supported adsorbent cartridge 141 containing adsorbent sheets 30 in which multiple stakes 142 and 143 (8 in the embodiment depicted in FIG. 3a) are driven into the adsorbent cartridge to securely hold the chemically reactive adsorbent sheets together. A volume 145 demarcated by dashed lines is removed from adsorbent cartridge 141 in FIG. 3a to expose stakes 142 and 143. These stakes enable the cartridge to maintain its correct external dimensions while simultaneously holding each sheet against the adjacent sheets. Alternatively, the adsorbent sheets can be staked with a staple or staples, a wire, rod(s), a cord, rivet(s), or elastic materials. The rigid staked cartridge may be further wrapped with a thin polymer sleeve such that the sleeve does not cover air inlet and outlet faces 146, 147 of the adsorbent cartridge. This thin sleeve prevents the end user from contacting the adsorbent chemical. The sleeve provides little or no clamping forces to hold the adsorbent cartridge together.

In some embodiments no polymer sheet is wrapped around the cartridge. The stakes rigidly hold the sheets in place such that sheet to sheet contact is maintained. As shown in FIG. 3(a) stakes 142 are inserted perpendicular to flow path 144 and additional cartridge stability can be achieved by inserting a stake or multiple stakes 143 at angles up to at 90 degrees with respect to flow path 144, which reduce or eliminate flexing of the cartridge. Air inlet face 146 and air outlet face 147 of cartridge 141 can be reversed should the direction of flow 144 be reversed. Cartridge 141 functions similarly for airflow from both directions.

Cartridge 141 can further include a wrap of polymer foam on four sides of the cartridge to allow for sealing when cartridge 141 is installed into a canister. The polymer foam could be installed by itself or over or under a polymer wrap.

Manufacture of Adsorbent Cartridges Having a Color Indicator

Figure 4:
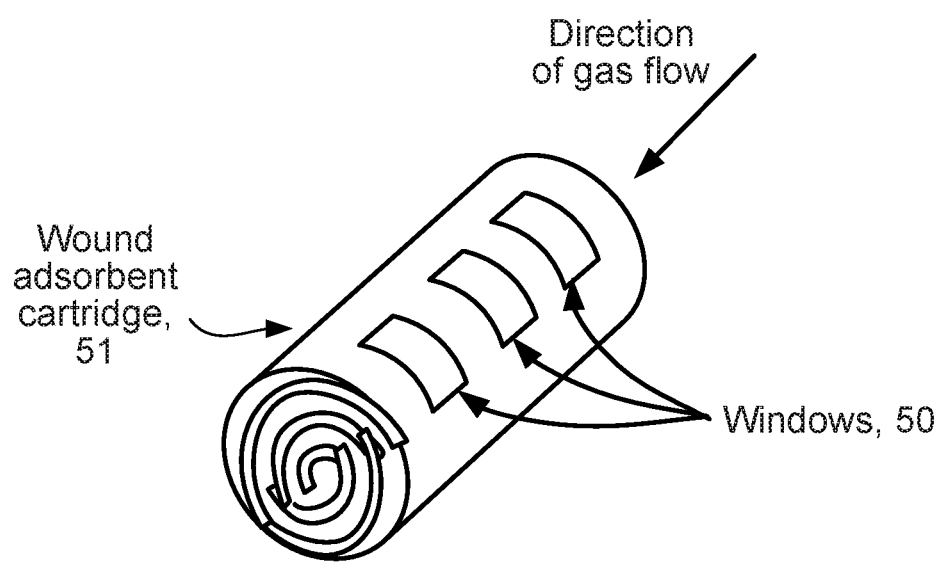
FIG. 4 depicts an adsorbent cartridge having a wound adsorbent sheet having windows cut in the outermost layer for viewing a color indicator applied to the layer beneath the outermost layer of the cartridge.

In some embodiments, any number of windows (or openings) may be cut into the outermost layer of the adsorbent ("outermost layer"), in any configuration. There may be a single line of windows (50) cut into the outermost layer of the wound adsorbent sheet of the cartridge (51) in the direction of gas flow in a straight line (FIG. 4), staggered, or a two-dimensional checkerboard of windows, straight or staggered, or some combination thereof. The windows may be of any dimension and each window may have its own dimension, independent of other windows. In one embodiment of the present invention, the windows are aligned with the direction of flow, and the window size is enlarged to provide for less adsorbent mass in the channels thereby increasing the $CO_2$ contaminant levels further down the cartridge, which provides for the ability to "tune" the time at which the indicator reacts and changes color.

Figure 5:
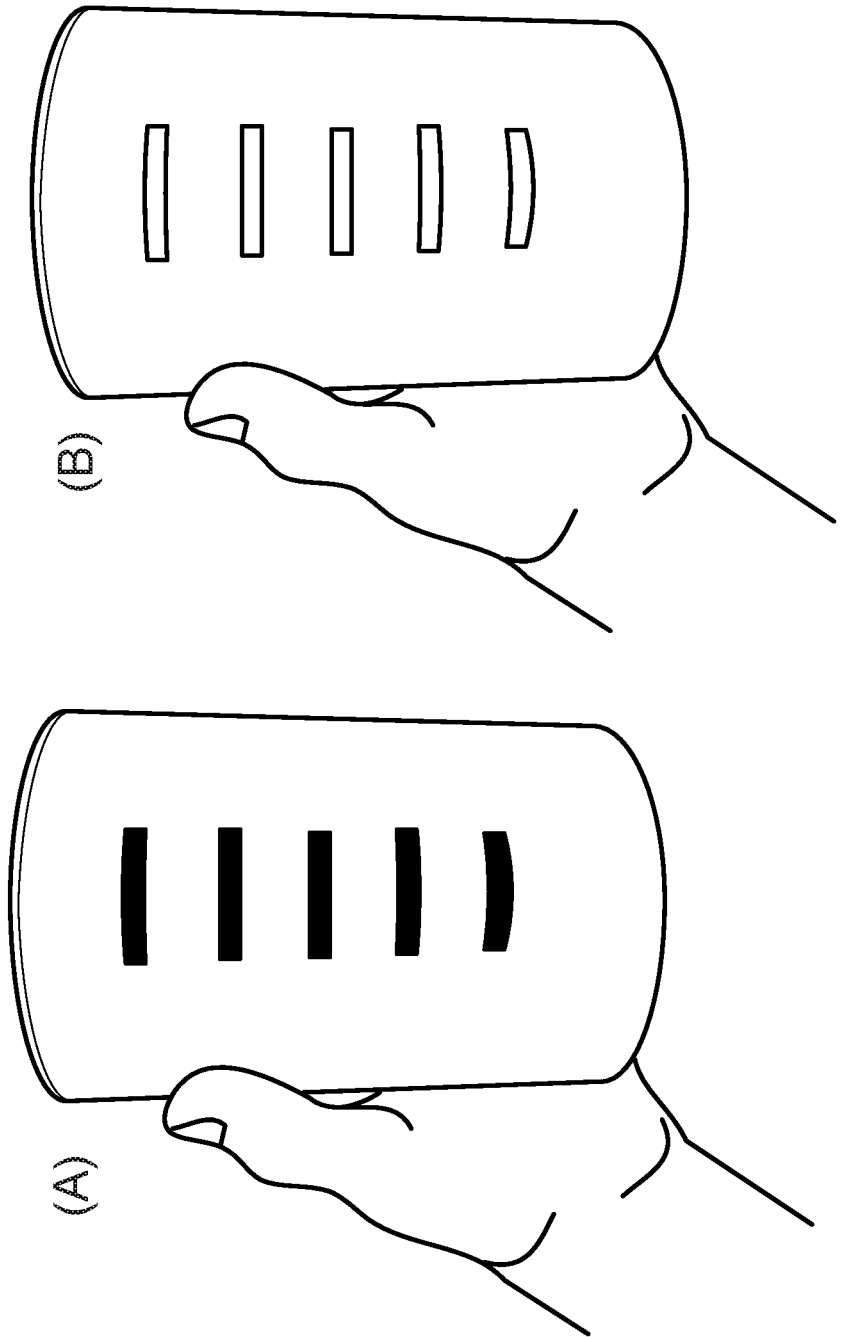
FIG. 5(a)-(b) depict an adsorbent cartridge having a wound adsorbent sheet having windows cut in the outermost layer where ethyl violet indicator has been applied to the layer beneath the outermost layer of the cartridge. The indicator is initially purple (FIG. 5(a)), but turns clear once in contacts the sodium hydroxide in the cartridge (FIG. 5(b)).

Once the windows have been cut in the outermost layer, indicator may be positioned on the adsorbent layer below the window in a variety of ways. A liquid coating of indicator may be applied to the layer beneath the outermost layer below the window, in an area larger than the window. For example, a solution of roughly 1% ethyl violet and 0.05% NaOH in water can be coated using a variety of methods using loadings from 1 to 20 mg/cm$^2$. This application may turn violet on exposure to the basic surface of a typical adsorbent (e.g., calcium hydroxide and 0.7 w/w % NaOH on a dry basis), but may turn back to the original white color of the adsorbent in less than a day (FIG. 5).

Instead of coating indicator on the layer beneath the window, one can place a thin indicator layer below the window. The thin indicator layer should be thin so as to not make the wound cartridge out of round, or to create a bump in an orthogonal stack of adsorbent sheets. It may be 30 mils or less or 20 mils or less, preferably 10 mils or less, In another embodiment, the area below the window can be at least partially filled with a plug of indicating material. This is similar to the indication layer approach, but in this case the plug has the same areal dimensions as the window. The plug may not be as thick as the layer that the window was cut out of.

In both the indicator layer and indicator plug embodiments, the indicator layer or plug may be composed of materials different from the adsorbent sheet layer. One example of the utility of this approach is to utilize the ethyl violet indicator dye in combination with calcium hydroxide and sodium hydroxide absorbent to make the plugs, which are the inserted into windows in a cartridge composed of lithium hydroxide, thereby getting the cartridge performance of a lithium hydroxide cartridge, with the indicator chemistry of the calcium hydroxide/ethyl violet.

It is also possible to use other indicator materials for calcium hydroxide or lithium hydroxide carbon dioxide adsorbents. As described in U.S. Pat. No. 3,068,073, activated alumina with thymol blue can be used to indicate the presence of carbon dioxide. Likewise U.S. Pat. No. 5,124,129 describes a carbon dioxide indicator based on hydrophilic polymer and the pH sensitive dye, o-cresolpthalein.

In all embodiments with windows (indicator coating, indicator layer and indicator plug), an outer transparent wrap may be placed over the outermost layer of adsorbent sheet to hold the indicator in or under the window, and it is transparent so the indicator can be seen without gas escaping from the windows or plugged areas.

In another embodiment, stripes or other discontinuous geometric patterns can be coated onto the surface of the outer adsorbent layer of the cartridge.

The chemistry of the indicator system of the present invention can be varied for any of the diverse applications. $CO_2$ adsorbents currently use a variety of indicators, such as ethyl violet, Titan yellow, Kenazol yellow, and the like. All of these indicators change with either the pH of the calcium hydroxide absorbent, which gets lower as the adsorbent is reacted, or by the dryness or water content of the adsorbent which is reduced after reacting with $CO_2$.

Other indicators that are used in other industrial applications may be utilized in the present invention, and include but are not limited to other specialty gas filtration application such as adsorbing water (U.S. Pat. No. 5,766,312), nitrogen, hydrogen, oxygen, petroleum processes and other industrial gas and liquid applications.

The present invention may also be used with adsorbent/indicator systems for hazardous materials as described in U.S. Pat. No. 4,326,514.

EXAMPLES

Example 1

Figure 2:
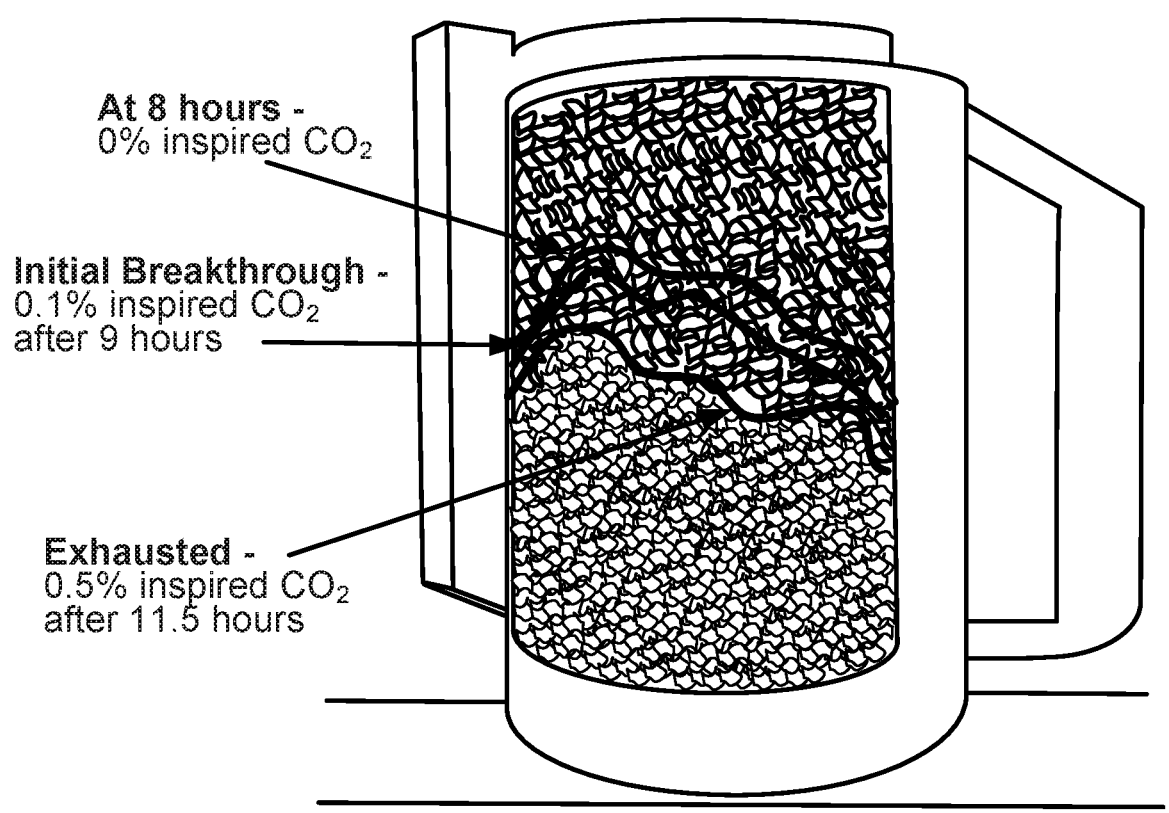
FIG. 2 depicts channeling of a color indicator in a granule-based adsorbent system.

An extruded sheet (thickness 51 mils) with ribs (height 29 mils) was made using calcium hydroxide and 0.7 w/w % NaOH and 2.5 w/w % $CaCl_2$ (dry basis), as described in U.S. Pat. No. 5,964,221). The sheet was wound into a cylindrical cartridge with dimensions 9.5 cm in diameter and 15 cm in height. The sheet was sprayed with ethyl violet indicator (1 w/w % in water). This cartridge was placed in a Micropore Stein housing (PN Rx0719a) designed to distribute airflow uniformly across the cartridge inlet end. This was tested at conditions representing a typical surgery: 10 liter/min tidal volume, 1 liter/min fresh gas flow, 10 breaths/minute, 1:2 inspiratory/expiratory, 160 cc $CO_2$/min). Photographs during the test demonstrate the superior uniformity of flow front within an adsorbent cartridge (FIG. 6) compared with a granular bed (FIG. 2).

Example 2

Figure 7:
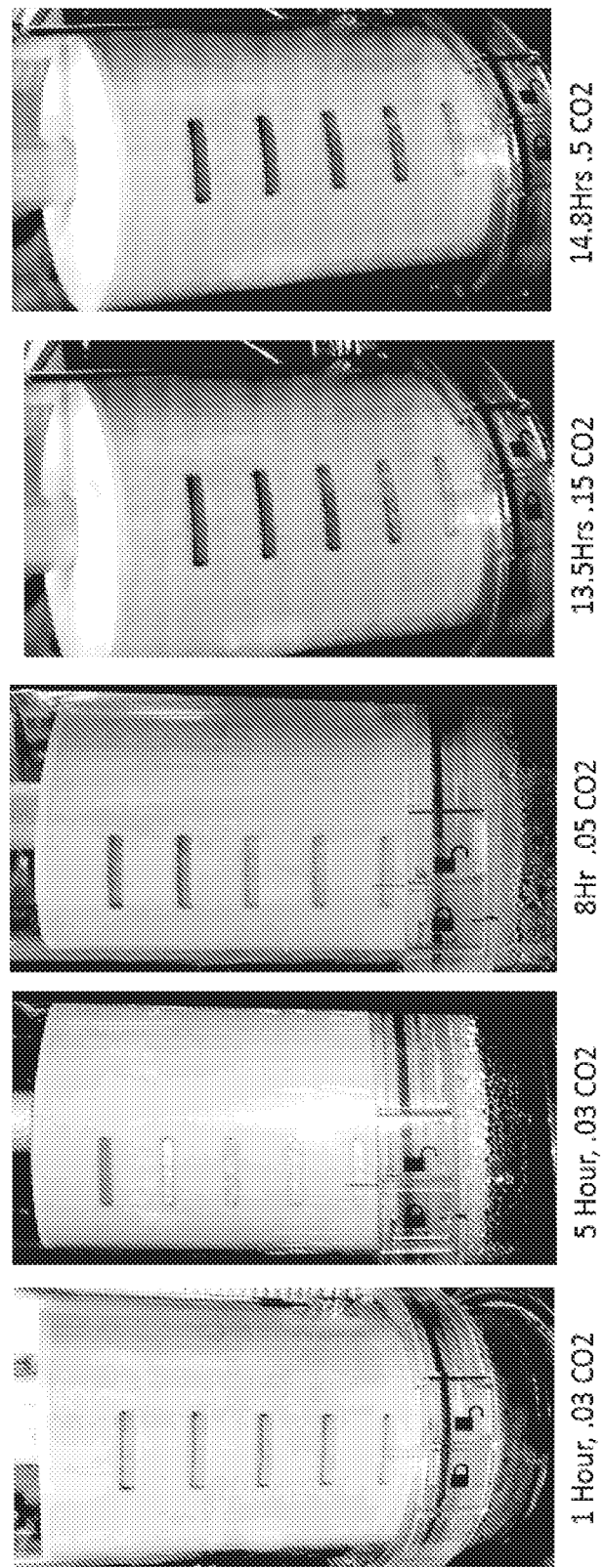
FIG. 7 depicts an adsorbent cartridge having a wound adsorbent sheet having windows cut in the outermost layer where ethyl violet indicator has been applied to the layer beneath the outermost layer of the cartridge, after exposure to carbon dioxide 1, 5, 8 13.3, and 14.8 hours.
Figure 8:
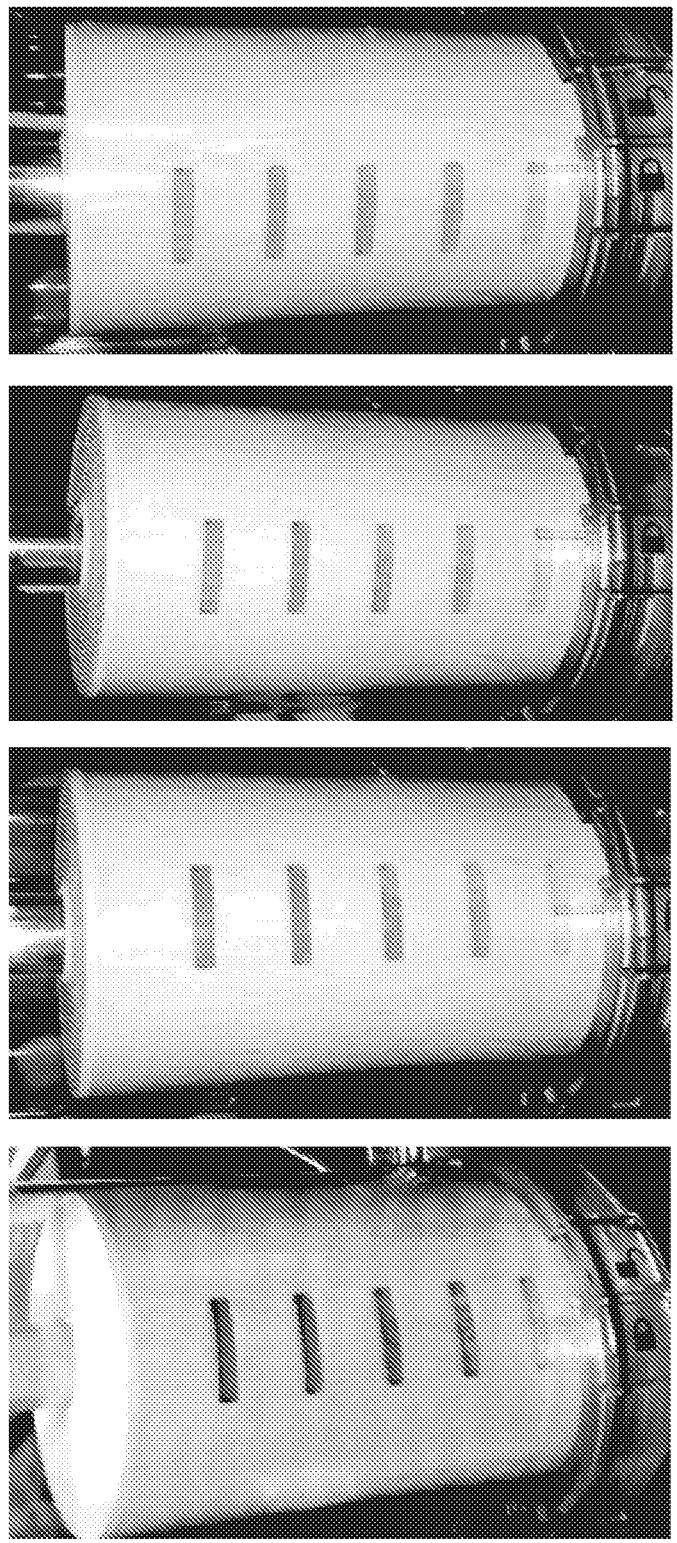
FIG. 8 depicts the adsorbent cartridge from FIG. 7 at 0, 22, 42, and 75 hours after the test, showing that the color change does not quickly revert.

A cylindrical adsorbent cartridge was prepared as per the instructions of Example 1, but it was loaded with 19 w/w % water as it was wound by spraying 34 Mg/cm2 of water on the rib side as it was wound. An outer transparent layer was wrapped around the outside to hold the end of the outer wrap and the cartridge was allowed to sit for two days so that the water could thoroughly wet the adsorbent. The outer transparent layer was then cut, the outermost layer was peeled back and a series of five windows was cut into the outer wrap. Ethyl violet (1 w/w % in water) was applied to an area below the windows, on the layer beneath the outermost layer. The loading of the ethyl violet solution was in the range of approximately 0.5-10 mg/cm2. The outer wrap was rewound and covered again with a transparent layer to hold it down (FIG. 5a). After 24 hours, the indicator turns white, which means the cartridge is ready for use (FIG. 5b). The cartridge was tested as described in Example 1 and photographs were taken during the test, demonstrating how the windows turn color as the adsorbent in the cartridge is consumed (FIG. 7). Four of the five windows turned color by the time the test ended (outlet $CO_2$ concentration 0.5%). Note that the indicator color did not revert for at least 75 hours (FIG. 8).

Embodiments

1. An adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use.

2. An adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of the visually exposed areas of color indicator are equal to or less than the total surface area of the outermost layer of the cartridge.

3. An adsorbent cartridge for removing gaseous carbon dioxide contaminants, comprising a self-supporting adsorbent sheet wound into a roll to form multiple layers mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of all color indicator in the cartridge is equal to or less than the total surface area of the outermost layer of the cartridge and wherein the total surface area of the visually exposed areas of color indicator is equal to or less than the total surface area of all color indicator in the cartridge.

4. The adsorbent cartridge of claim 3 or 4, wherein the total surface area of all color indicator in the cartridge is 0.05% to 50% of the surface area of the outermost layer.

5. The adsorbent cartridge of claim 3 or 4, wherein the color indicator is applied to one or more layers of the cartridge solely on the outer side of the adsorbent sheet, wherein one or more discrete areas of color indicator are visible to external observer or are exposed visually to an external observer through windows cut into the outermost layer.

6. The adsorbent cartridge of claim 3 or 4, wherein the color indicator is applied to an indicator layer sandwiched between the outermost layer and the layer beneath the outermost layer, wherein one or more discrete areas of color indicator are exposed visually to external observer through windows cut into the outermost layer.

7. The adsorbent cartridge of claim 3 or 4, wherein the color indicator is applied to a plug of material at least partially filling one or more windows cut into the outermost layer, thereby visually exposing one or more discrete areas of color indicator to an external observer.

8. The adsorbent cartridge of any one of claims 1-7, wherein the cartridge is for use in an anesthesia breathing circuit.

9. The adsorbent cartridge of any one of claims 1-8, wherein the multiple layers are mechanically spaced by parallel, longitudinal ribs molded out of the sheet.

10. The adsorbent cartridge of any one of claims 1-8, wherein the layers are mechanically spaced by additional spacer material.

11. The adsorbent cartridge of any one of claims 1-10, wherein the adsorbent material comprises calcium hydroxide.

12. The adsorbent cartridge of any one of claims 1-10, wherein the adsorbent material comprises lithium hydroxide.

13. The adsorbent cartridge of any one of claims 1-13, wherein the adsorbent material further comprises sodium hydroxide, potassium hydroxide, calcium chloride, or lithium hydroxide.

14. The adsorbent cartridge of any one of claims 1-14, further comprising a transparent film covering the outermost layer of the cartridge.

15. The adsorbent cartridge of any one of claims 1-15, wherein the color indicator comprises ethyl violet, Titan yellow, Kenazol yellow, activated alumina with thymol blue, or o-cresolpthalein.

16. The adsorbent cartridge of claim 5, wherein the adsorbent material comprises calcium hydroxide and wherein the one or more discrete areas of color indicator visible to external observer are applied to the outermost layer of the cartridge.

17. The adsorbent cartridge of claim 16, wherein the multiple layers are mechanically spaced by parallel, longitudinal ribs molded out of the sheet.

18. The adsorbent cartridge of claim 16 or 17, wherein the color indicator comprises ethyl violet, Titan yellow, Kenazol yellow, activated alumina with thymol blue, or o-cresolpthalein.

19. The adsorbent cartridge of claim 16 or 17, wherein the color indicator comprises ethyl violet.

20. The adsorbent cartridge of any one of claims 16-19, wherein the cartridge is for use in an anesthesia breathing circuit.

21. The adsorbent cartridge of claim 5, wherein the adsorbent material comprises calcium hydroxide and wherein the color indicator is applied to the layer beneath the outermost layer of the cartridge and the one or more discrete areas of the color indicator are exposed visually to the external observer by windows cut in the outermost layer of the cartridge.

22. The adsorbent cartridge of claim 21, wherein the multiple layers are mechanically spaced by parallel, longitudinal ribs molded out of the sheet.

23. The adsorbent cartridge of claim 21 or 22, wherein the color indicator comprises ethyl violet, Titan yellow, Kenazol yellow, activated alumina with thymol blue, or o-cresolpthalein.

24. The adsorbent cartridge of claim 21 or 22, wherein the color indicator comprises ethyl violet.

25. The adsorbent cartridge of any one of claims 21-24, wherein the cartridge is for use in an anesthesia breathing circuit.

26. The adsorbent cartridge of claim 6, wherein the multiple layers are mechanically spaced by parallel, longitudinal ribs molded out of the sheet.

27. The adsorbent cartridge of claim 26, wherein the color indicator comprises ethyl violet, Titan yellow, Kenazol yellow, activated alumina with thymol blue, or o-cresolpthalein.

28. The adsorbent cartridge of claim 27, wherein the color indicator comprises ethyl violet.

29. The adsorbent cartridge of any one of claims 26-28, wherein the cartridge is for use in an anesthesia breathing circuit.

30. The adsorbent cartridge of any one of claims 26-29, wherein the indicator layer is 30 mils or less in thickness.

31. The adsorbent cartridge of any one of claims 26-29, wherein the indicator layer is 20 mils or less in thickness.

32. The adsorbent cartridge of any one of claims 26-29, wherein the indicator layer is 10 mils in thickness.

33. The adsorbent cartridge of any one of claims 26-32, wherein the indicator layer is formed from a mixture comprising calcium hydroxide, sodium hydroxide, and a polymer, to which the color indicator has been applied.

34. The adsorbent cartridge of claim 33, wherein the color indicator is ethyl violet.

35. The adsorbent cartridge of claim 33 or 34, wherein the adsorbent material comprises lithium hydroxide.

36. The adsorbent cartridge of claim 26, having a single window, wherein the indicator layer has a single discrete area of the color indicator positioned to center on the window in the outermost layer of the cartridge.

37. The adsorbent cartridge of claim 36, wherein the indicator layer is formed from a mixture of calcium hydroxide, sodium hydroxide, and a polymer, to which the discrete area of color indicator has been applied.

38. The adsorbent cartridge of claim 37, wherein the color indicator is ethyl violet.

39. The adsorbent cartridge of claim 38, wherein the adsorbent material comprises lithium hydroxide.

40. The adsorbent cartridge of claim 26, having multiple windows, wherein the indicator layer has multiple discrete areas of the color indicator positioned to center on the windows in the outermost layer of the cartridge.

41. The adsorbent cartridge of claim 40 wherein the indicator layer is formed from a mixture of calcium hydroxide, sodium hydroxide, and a polymer, to which the discrete areas of color indicator have been applied.

42. The adsorbent cartridge of claim 41, wherein the color indicator is ethyl violet.

43. The adsorbent cartridge of claim 42, wherein the adsorbent material comprises lithium hydroxide.

44. The adsorbent cartridge of claim 26, having multiple windows, wherein the indicator layer is a strip positioned such that the area exposed by each window is covered by said strip, thereby exposing the color indicator to said external observer.

45. The adsorbent cartridge of claim 44, wherein the strip is formed from a mixture of calcium hydroxide, sodium hydroxide, and a polymer, to which the color indicator has been applied.

46. The adsorbent cartridge of claim 45, wherein the color indicator is ethyl violet.

47. The adsorbent cartridge of claim 46, wherein the adsorbent material comprises lithium hydroxide.

48. The adsorbent cartridge of claim 26, having multiple windows, wherein a separate indicator layer patch is utilized for each window.

49. The adsorbent cartridge of claim 48, wherein the indicator layer is formed from a mixture of calcium hydroxide, sodium hydroxide, and a polymer, to which the discrete areas of color indicator have been applied.

50. The adsorbent cartridge of claim 49, wherein the color indicator is ethyl violet.

51. The adsorbent cartridge of claim 50, wherein the adsorbent material comprises lithium hydroxide.

52. The adsorbent cartridge of claim 7, wherein the multiple layers are mechanically spaced by parallel, longitudinal ribs molded out of the sheet.

53. The adsorbent cartridge of claim 52, wherein the plug has the same areal dimensions as each window.

54. The adsorbent cartridge of claim 53, wherein the indicator layer is formed from a mixture of calcium hydroxide, sodium hydroxide, and a polymer, to which the color indicator has been applied.

55. The adsorbent cartridge of claim 54, wherein the color indicator is ethyl violet.

56. The adsorbent cartridge of claim 54, wherein the color indicator comprises Titan yellow, Kenazol yellow, activated alumina with thymol blue, or o-cresolpthalein.

57. The adsorbent cartridge of 55 or 56, wherein the adsorbent material comprises lithium hydroxide.

58. The adsorbent cartridge of any one of claims 52-57, wherein the plug is 0.004 to 0.1 in thickness.

59. The adsorbent cartridge of any one of claims 16-58, further comprising a transparent film covering the outermost layer of the cartridge.

60. An adsorbent cartridge for removing gaseous carbon dioxide contaminants, comprising a stack of self-supporting adsorbent sheets mechanically spaced to provide gas flow channels between the layers from one end of the cartridge to the other, wherein the sheet is formed from a mixture comprising polymer and an adsorbent material comprising calcium hydroxide or lithium hydroxide, wherein the cartridge further comprises a color indicator for visually indicating consumption of the adsorbent to an external observer, wherein at least one area of color indicator is visually exposed to an external observer while the cartridge is in use, wherein the total surface area of all color indicator in the cartridge is equal to or less than the total surface area of the outermost layer of the cartridge and wherein the total surface area of the visually exposed areas of color indicator is equal to or less than the total surface area of all color indicator in the cartridge.

A number of embodiments of the invention have been described. Nevertheless, it will be understood that various modifications may be made without departing from the spirit and scope of the invention. Accordingly, other embodiments are within the scope of the following claims.

What is claimed is:

1. An adsorbent cartridge for removing gaseous contaminants, comprising layers of one or more self-supporting adsorbent sheets mechanically spaced to provide gas flow channels between the layers from one end of the cartridge to the other, wherein the cartridge further comprises a color indicator for visually indicating consumption of the adsorbent to an external observer, wherein at least one area of color indicator is visually exposed to the external observer while the cartridge is in use, and wherein the color indicator is visually exposed by one or more windows cut into a side or an outermost layer of the adsorbent sheets of the adsorbent cartridge.

2. The adsorbent cartridge of claim 1, wherein the cartridge is formed from a single self-supporting adsorbent sheet wound into a roll to form multiple layers.

3. The adsorbent cartridge of claim 1, wherein the cartridge is formed from a stack of the self-supporting adsorbent sheets.

4. The adsorbent cartridge of claim 1, wherein the sheet is formed from a mixture comprising an adsorbent material.

5. The adsorbent cartridge of claim 4, wherein the sheet is formed from a mixture comprising polymer and the adsorbent material.

6. The adsorbent cartridge of claim 4, wherein the adsorbent material comprises calcium hydroxide or lithium hydroxide.

7. The adsorbent cartridge of claim 1, wherein the total surface area of all color indicator in the cartridge is 0.05% to 50% of the surface area of the outermost layer.

8. The adsorbent cartridge of claim 1, wherein the color indicator is applied to one or more layers of the cartridge solely on an outer side of the adsorbent sheet, wherein one or more discrete areas of color indicator are visible to the external observer or are exposed visually to the external observer through windows cut into the outermost layer.

9. The adsorbent cartridge of claim 1, wherein the color indicator is applied to an indicator layer sandwiched between the outermost layer and the layer beneath the outermost layer, wherein one or more discrete areas of color indicator are exposed visually to the external observer through windows cut into the outermost layer.

10. The adsorbent cartridge of claim 1, wherein the color indicator is applied to a plug of material at least partially filling one or more windows cut into the outermost layer, thereby visually exposing one or more discrete areas of color indicator to the external observer.

11. The adsorbent cartridge of claim 1, wherein the color indicator is applied to the layer beneath the outermost layer of the cartridge and the one or more discrete areas of the color indicator are exposed visually to the external observer by windows cut in the outermost layer of the cartridge.

12. The adsorbent cartridge of claim 9, wherein the indicator layer can be a strip to which the color indicator is applied.

13. The adsorbent cartridge of claim 9, having multiple windows, wherein the indicator layer is a strip positioned such that the area exposed by each window is covered by said strip, thereby exposing the color indicator to said external observer.

14. The adsorbent cartridge of claim 12, wherein the strip is formed from a mixture of calcium hydroxide, sodium hydroxide, and a polymer, to which the color indicator has been applied.

15. The adsorbent cartridge of claim 1, wherein the cartridge is for use in an anesthesia breathing circuit.

16. The adsorbent cartridge of claim 1, wherein the layers are mechanically spaced by parallel, longitudinal ribs molded out of the sheet.

17. The adsorbent cartridge of claim 1, wherein the color indicator comprises ethyl violet, Titan yellow, Kenazol yellow, activated alumina with thymol blue, or o-cresolpthalein.

18. The adsorbent cartridge of claim 13, wherein the strip is formed from a mixture of calcium hydroxide, sodium hydroxide, and a polymer, to which the color indicator has been applied.

* * * * *

UNITED STATES PATENT AND TRADEMARK OFFICE
CERTIFICATE OF CORRECTION

PATENT NO. : 10,994,091 B2
APPLICATION NO. : 16/343705
DATED : May 4, 2021
INVENTOR(S) : Douglas B. McKenna, Vince Suddard and Glenn Shealy Page 1 of 1

It is certified that error appears in the above-identified patent and that said Letters Patent is hereby corrected as shown below:

In the Claims

Column 32, Lines 12-13, Claim 17, delete "o-cresolpthalein." and insert -- o-cresolphthalein. --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*